US006998567B2

(12) United States Patent
Yeik

(10) Patent No.: US 6,998,567 B2
(45) Date of Patent: Feb. 14, 2006

(54) GENERATION AND APPLICATION OF EFFICIENT SOLID-STATE LASER PULSE TRAINS

(75) Inventor: Glenn Yeik, Lake Forest, CA (US)

(73) Assignee: Trimedyne, Inc., Irvine, CA (US)

( * ) Notice: Subject to any disclaimer, the term of this patent is extended or adjusted under 35 U.S.C. 154(b) by 333 days.

(21) Appl. No.: 10/355,952

(22) Filed: Jan. 31, 2003

(65) Prior Publication Data

US 2004/0151217 A1 Aug. 5, 2004

(51) Int. Cl.
*B23K 26/36* (2006.01)

(52) U.S. Cl. ............................... 219/121.61; 219/121.83
(58) Field of Classification Search .............. 219/121.6, 219/121.61, 121.62, 121.67–121.69, 121.78, 219/121.83; 372/25, 35, 69; 606/4–6, 10–12; 351/209, 211

See application file for complete search history.

(56) References Cited

U.S. PATENT DOCUMENTS 4,785,456 A * 11/1988 Kaplan .................... 372/38.09
6,156,030 A * 12/2000 Neev ........................... 606/10
6,193,711 B1 * 2/2001 Connors et al. .............. 606/12
6,210,401 B1 * 4/2001 Lai .............................. 606/12

* cited by examiner

*Primary Examiner*—Samuel M. Heinrich
(74) *Attorney, Agent, or Firm*—Olson & Hierl, Ltd.

(57) ABSTRACT

A method and devices for generating laser pulse trains for delivery to a target including the use of a single laser generator which produces a plurality of pulse groupings of two or more individual laser pulses within each laser pulse train, generated at selected time intervals. The time intervals between the individual pulses within each of the pulse groupings along with the intervals between pulse groupings themselves are selected and controlled by a controller in reference to several variables including the emission and energy storage lifetimes of the lasing medium, the thermal diffusion time constant of the target, the time required to cool the target after the application of laser pulses to its ambient temperature, and the dissipation time of acoustic waves generated by the pulses.

11 Claims, 7 Drawing Sheets

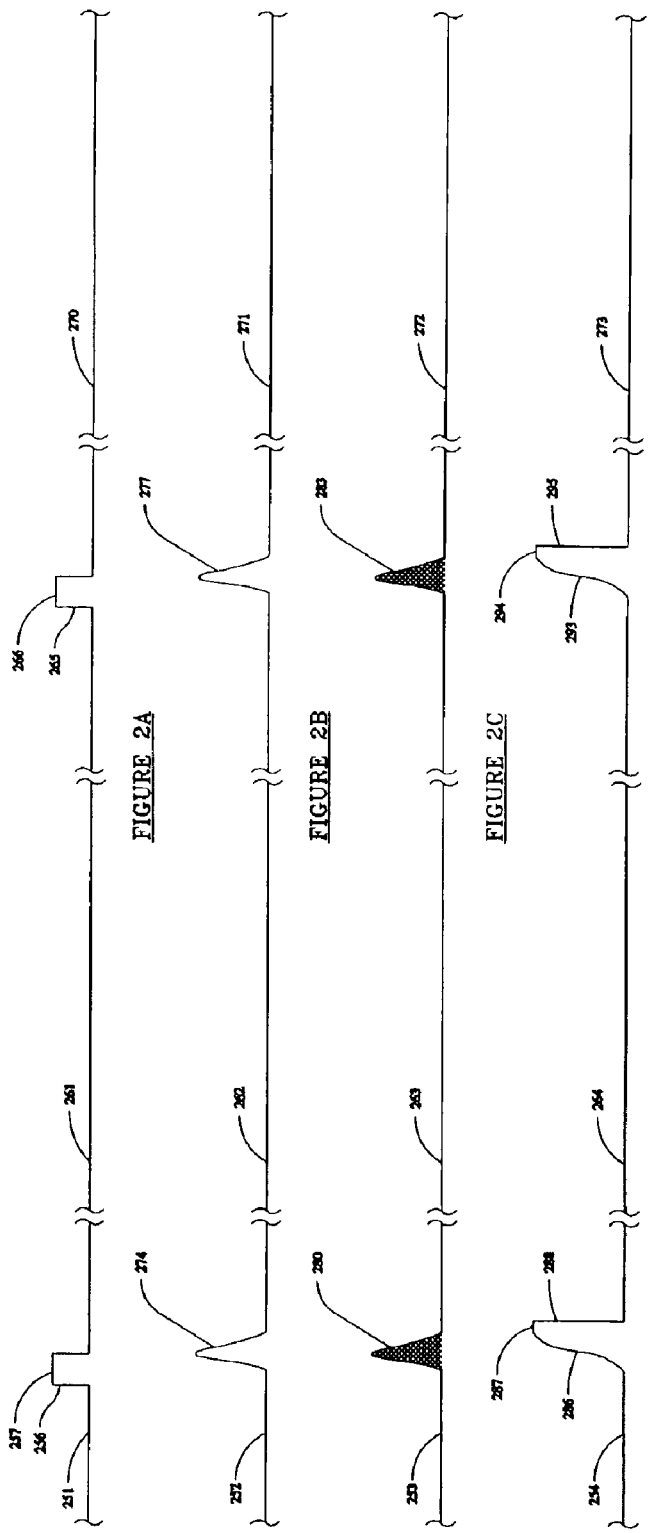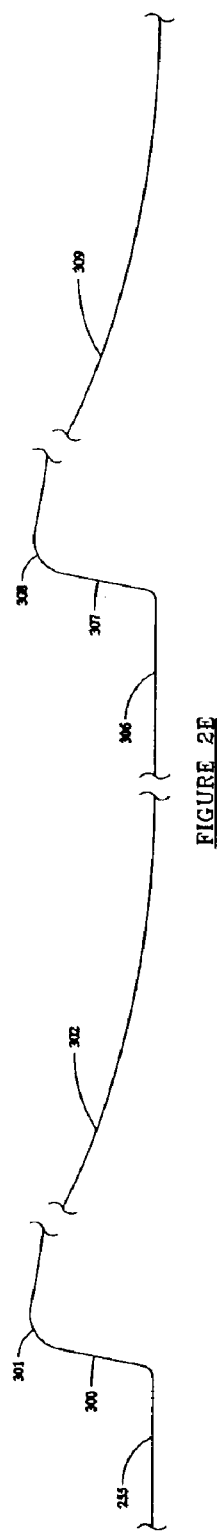

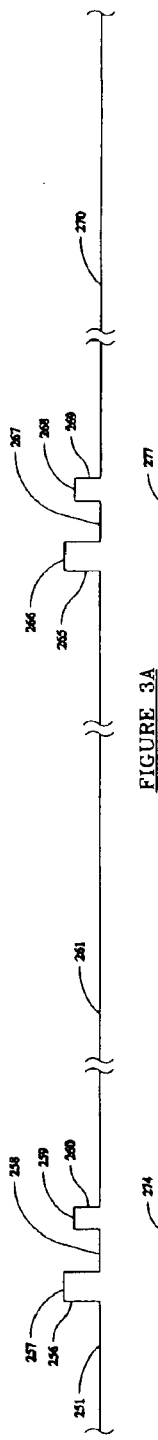
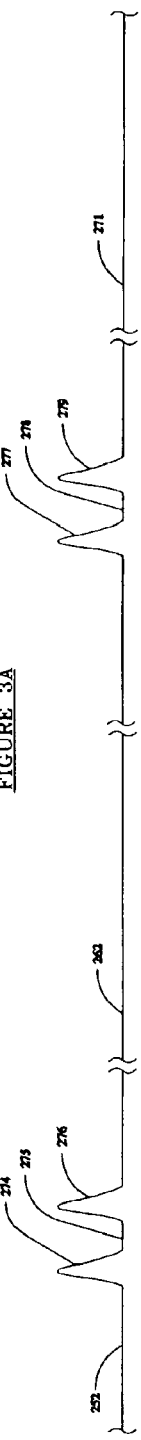
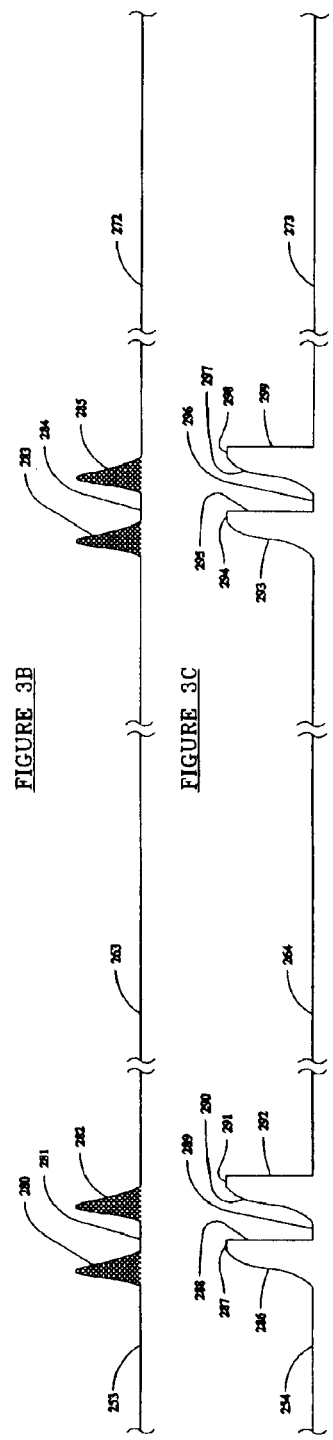
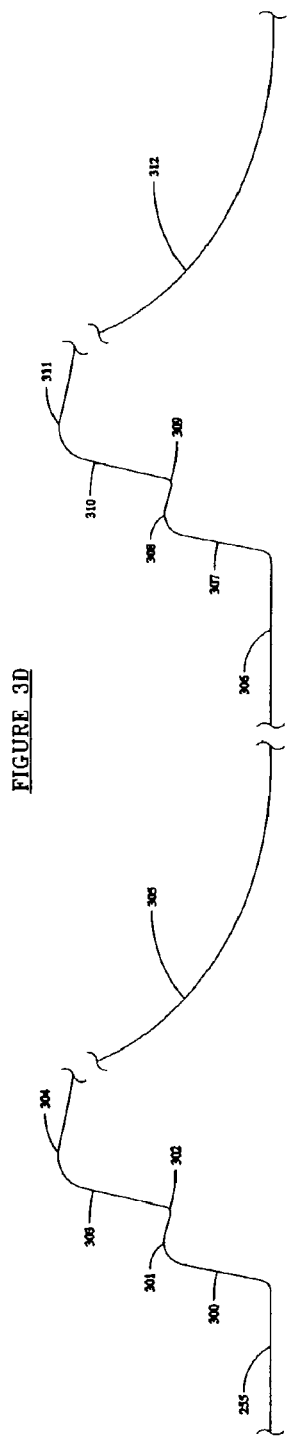
FIGURE 3A
FIGURE 3B
FIGURE 3C
FIGURE 3D
FIGURE 3E

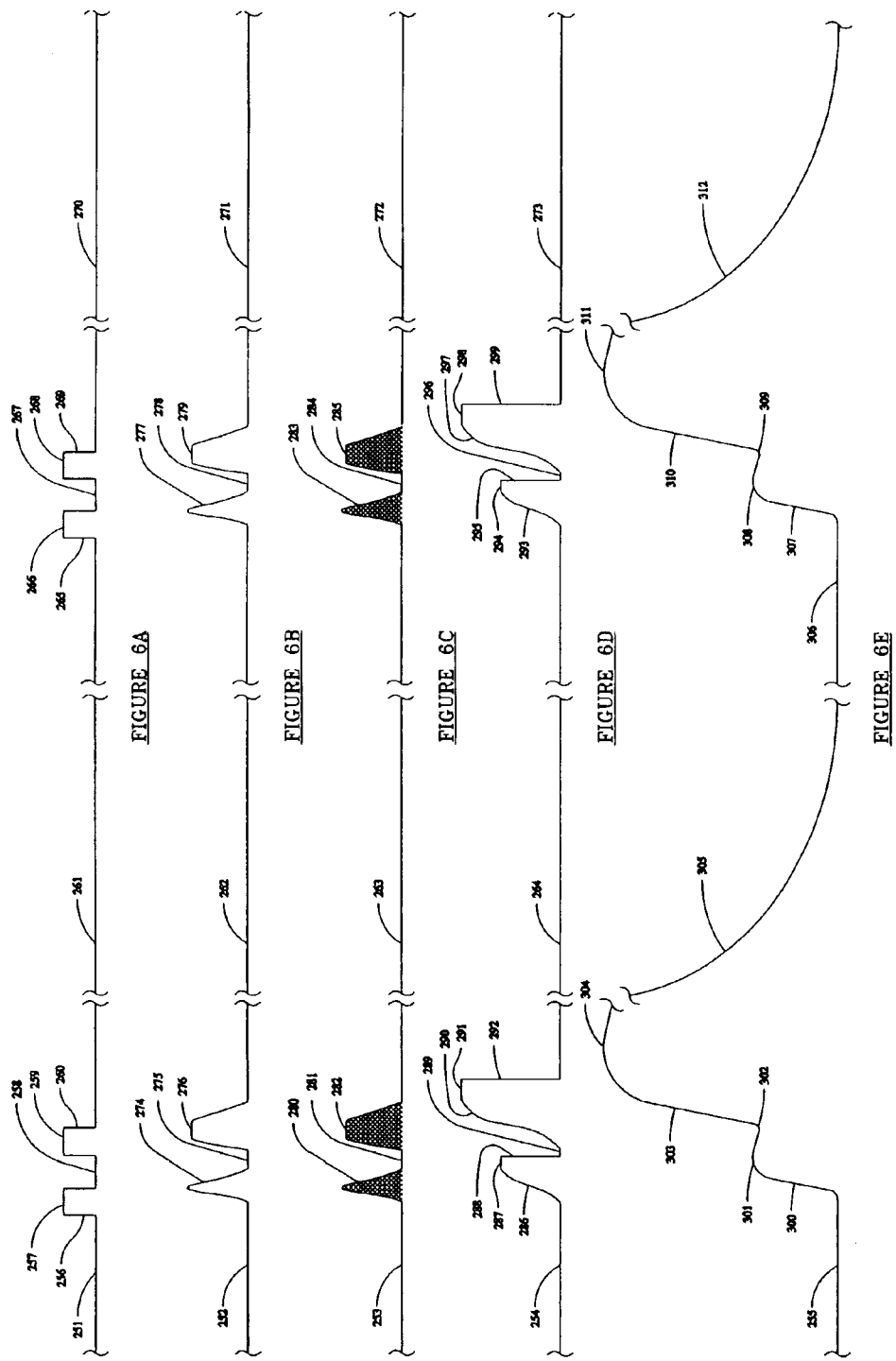

GENERATION AND APPLICATION OF EFFICIENT SOLID-STATE LASER PULSE TRAINS

TECHNICAL FIELD

The present invention relates to laser devices and lasing methods and, more particularly, to a method for the generation and application of laser pulse trains with pulse groupings using selected solid-state lasing media.

BACKGROUND OF THE INVENTION

Various lasers have been developed for engraving, cutting, welding, annealing, etc. various materials. Lasers have also been developed or proposed for delivering laser energy to a site or target on or in a mammalian body for diagnostic or therapeutic purposes. These lasers typically deliver laser energy to a target site either directly or through delivery devices such as an articulated arm, a hollow waveguide or a flexible optical fiber. If pulsed laser energy is desired in these applications, it is usually provided in a train of evenly spaced pulses.

In therapeutic veterinary or medical applications, laser energy is used to produce a desired effect on various types of tissue. The laser energy interacts with the tissue through reflection, refraction or absorption. This interaction may be used to perform incision, excision, resection, vaporization, ablation, coagulation, hemostasis, and denaturization of various tissues. One or more of the above effects of laser radiation on tissue may be produced with pulses of laser radiation having, for example, a wavelength of about 2,100 nm, a pulse width of about 300 microseconds and an energy density of about 1 $J/cm^2$ incident on the target site. Laser energy of this wavelength is highly absorbed by water, a constituent of virtually all tissues.

The effect of laser radiation on tissue is dependent upon several factors, some of which include the type of tissue irradiated, the amount of radiation absorbed by the tissue, the time during which the laser energy is delivered and the absorption efficiency of the wavelength of laser energy on the target tissue. Relatively hard or dense tissues, such as calcified tissues or bone which may have a comparatively low water content, require relatively high energy levels for effective ablation. For example, at a wavelength of about 2,100 nm, this would optimally require an energy density of 1 to 20,000 J/cm at a pulse width of 100 to 800 $\mu s$ at the target tissue site.

In a variety of applications, including surgical procedures, where ablation, vaporization or other effects are desired, it is preferred to achieve these effects relatively quickly to reduce thermal conduction and damage to nearby tissues. Also, in these applications, it may be desirable to increase the time period between pulses, to allow additional time for the target to cool between pulses. In order to ablate certain types of tissue quickly, the laser radiation incident at the site or target of application, for example, at a wavelength of about 2,100 nm, should preferably be delivered in pulses of 1 to 10 Joules of energy with a pulse width of 100 to 800 $\mu s$ at a repetition rate of 1 to 100 Hz.

The production of such high energy levels with a single laser resonator or oscillator (e.g. a source of high intensity optical radiation such as from a flash lamp, arc lamp or diode-laser, and a lasing medium) is difficult or impossible. This is especially true for thulium holmium:YAG, chromium thulium holmium:YAG, erbium:YAG, thulium:YAG, ruby or similar lasers having a limited energy output capability.

Many commercially available lasers that are suitable for ablation or vaporization of tissue cannot be operated for extended periods of time at such high energy levels, without creating excessive heat or placing excessive stress on the laser system and/or an optional optical delivery mechanism, which can lead to premature component failure.

Other methods of generating multiple consecutive laser pulses within a short period of time are known in the art and have previously been disclosed. However, the implementation of these methods requires an increased number of components, complexity, and cost compared to the present invention. Additionally, these other methods typically require more input power than the present invention in order to achieve the same target effects.

Accordingly, it would be desirable to provide an improved laser system capable of generating radiant energy at higher effective energy levels to the target site. Preferably, such an improved system should accommodate the use of commercially available, pulsed lasers of the following types: erbium:yttrium aluminum garnet (Er:YAG), thulium:yttrium aluminum garnet (Tm:YAG), thulium holmium:yttrium aluminum garnet (TmHo:YAG), chromium thulium holmium:yttrium aluminum garnet (CrTmHo:YAG), neodymium:yttrium aluminum garnet (Nd:YAG), alexandrite, ruby and other pulsed lasers.

Desirably, such an improved laser system should deliver radiant energy to a target with a relatively long thermal diffusion time or relatively low thermal conductivity (e.g. tissue, bone, hair, cotton, plastic, wood, etc.) in a pulse train that has a sufficiently high energy level during a relatively short time period in order to quickly raise its temperature to produce the desired effect on the target, while lengthening the time between pulses to allow additional time for the target to cool between pulses.

Conceptually, if this rapid target temperature rise is produced using a series or train of evenly spaced pulses of laser energy, the temperature of the target (e.g. bone, organs, cartilage, etc.) will start to decay back to its ambient temperature after the end of each pulse in this train. It is understood that the temperature of a target that has been raised above its ambient temperature $T_a$ to an elevated temperature $T_s$ after the end of each pulse in this train decreases ideally according to the following equation:

$$T_e = T_a + (T_s - T_a)e^{-t/k}$$

where $T_s$ is the maximum elevated temperature to which the tissue has been raised by a preceding pulse or pulses, e is the natural logarithm base, t is any selected time period following the achievement of temperature $T_s$, k is the target thermal diffusion time constant, and $T_e$ is the resulting time-dependent temperature at the end of time period t.

When a target (e.g. tissue) is subjected to a pulse of laser energy, the target temperature rises to a maximum temperature $T_s$, and then begins to decrease. If the maximum target temperature after the end of a pulse of laser energy $T_s$ were below the desired target temperature $T_d$, it would be desirable to provide increased energy to the target to allow the desired target temperature $T_d$ to be achieved. It is believed that the efficiency of laser effects (e.g. vaporization or ablation) on targets with a relatively long thermal diffusion time can be increased by subjecting the target to pulses of laser energy in a way that results in little or no temperature decay between laser pulses. Accordingly, to achieve this increased efficiency, the time span between consecutive laser pulses in the pulse train should be relatively short, preferably much shorter than the target thermal diffusion time constant.

For example, when a target site of a typical human tissue, such as muscle or cartilage, is elevated to an initial temperature of about 120° C., the tissue temperature decays to 115° C. in about 10 milliseconds. It would be desirable to subject the tissue to a plurality of laser pulses in less than or equal to that time period. A preferred laser system for the ablation or vaporization of such tissue should accommodate the emission of two or more laser pulses with a typical temporal separation of less than 10 milliseconds between the pulses, with a pulse separation time and pulse width that depend upon the desired peak pulse energy and target effects; for example, a pulse separation time of 1 ms and a pulse width of 100 to 800 µs at a wavelength of about 2,010 nm. The pulse separation and/or pulse width may vary significantly depending upon the specific application. For example, in order to ablate or fragment bladder, kidney, or ureteral stones, a pulse separation of 10 µs and a pulse width of 1–10,000 nanoseconds may be desirable.

As is previously known from many literature sources, many solid-state lasing ions exist, of which many are bivalent and trivalent lanthanides, for example, praseodymium ($Pr^{3+}$), neodymium ($Nd^{3+}$), samarium ($Sm^{2+}$), europium ($Eu^{3+}$), gadolinium ($Gd^{3+}$), terbium ($Tb^{3+}$), dysprosium ($Dy^{2+}$), holmium ($Ho^{3+}$), erbium ($Er^{3+}$), thulium ($Tm^{2+}$, $Tm^{3+}$) and ytterbium ($Yb^{3+}$). Other solid-state lasing ions are also well known, for example, titanium ($Ti^{3+}$), vanadium ($V^{2+}$), chromium ($Cr^{2+}$, $Cr^{3+}$ and $Cr^{4+}$) and others.

At, above, and/or below room temperature, there are many different host crystals that may be used in conjunction with many of the above solid-state lasing ions or combinations thereof, including, for example, $Y_3Al_5O_{12}$ (YAG), $Y_3Sc_2Ga_3O_{12}$ (YSGG), $LiYF_4$ (YLF), $Gd_3Sc_2Ga_3O_{12}$ (GSGG), $Y_3Ga_5O_{12}$ (YGG), $Y_3AlO_3$ (YAP), $LaF_3$, $BaY_2F_8$, $KCaF_3$ and others. Other solid-state host materials, such as plastics or gelatins, may also be used in conjunction with many solid-state lasing ions. The selection of a relatively transparent host material that is sensitized or doped with various relative percentage(s) of one or more lasing ion(s) determines the wavelength and other properties of the solid-state active lasing medium.

One or more lasing-related properties may be used to classify various solid-state lasing media. A subset of all available solid-state lasing media exhibit the characteristics of relatively long emission and energy storage lifetimes, for example, on the order of 100 µs or longer. Many of these types of solid-state lasing media are well known, for example, Er:YAG, Tm:YAG, Ho:YAG, Er:YSGG, Tm:YSGG, TmHo:YAG, CrTmHo:YAG, erbium-doped fiber amplifiers and others, and have been characterized as to both the predicted and actual characteristics of emission and energy storage lifetimes. The emission lifetime of these media are usually longer than the energy storage lifetime due to, for example, impurities in the lasing medium, constructional constraints imposed by the laser resonator design, sub-optimal thermal management and other factors. It would be desirable to utilize these properties to produce advantageous pumping and energy extraction and deliver a plurality of laser pulses within a short time period.

The present invention provides an improved laser energy generation system that can produce the above-discussed benefits and features.

SUMMARY OF THE INVENTION

The present invention provides a unique method and device for generating efficient laser pulse trains using selected solid-state lasing media for subjecting a target site to higher effective laser energy than is typically possible with normal laser pulsing modes for that same single lasing medium.

The present invention is suitable for use in a medical system in order to deliver radiant laser energy pulses to a selected tissue site in a desired, controlled manner. The invention is particularly well suited for use in surgical procedures for coagulating or cutting relatively soft tissues, as well as for rapidly vaporizing or ablating relatively hard tissues.

The device for generating laser pulse trains for delivery to a target is comprised of a single laser generator that generates a plurality of laser pulse groupings within a given pulse train at selected time intervals, wherein each of the laser pulse groupings is comprised of two or more successive individual laser pulses generated at selected time intervals. The method includes the step of delivering each laser pulse train to the target.

In one embodiment, the selected time intervals between the pluralities of laser pulse groupings are greater than the selected time intervals between the individual pulses within each of the pulse groupings. In another embodiment, the selected time interval between each of the laser pulse groupings is equal to the time required to cool the target back to its ambient temperature (thermal diffusion time). Depending upon the particular application, the selected time intervals between each of the individual pulses in each of the pulse groupings, and/or the time interval between laser pulse groupings, may also be either less than or greater than the thermal diffusion time of the target.

In a further embodiment, the selected time intervals between each of the individual pulses in each pulse grouping may be either less than or greater than the dissipation time of an acoustic shock wave generated by the preceding laser pulse in the respective pulse grouping.

The method of the present invention can also include the steps of controlling the time intervals between each of the pulse groupings within a given pulse train and controlling the shape, amplitude, duration, and/or interval of each of the individual pulses within each of the pulse groupings. Moreover, each of the pulse groupings may consist of first, second and subsequent individual laser pulses, where the energy of pump pulses needed to produce equivalent or greater second and subsequent laser pulses may be substantially less than the energy of the pump pulse needed to produce the first laser pulse in each of the laser pulse groupings.

The generator may be any one of several known generator sources such as, for example, a resonator, an oscillator or a continuous wave pump. A controller or controllers associated with the generator allow the time intervals between the individual pulses within each pulse grouping, as well as the time intervals between the plurality of pulse groupings, to be selected and controlled. The controller also selects and controls the amplitude, duration and shape of each of the pulses. Sensors associated with the controller allow the characteristics of both pulses generated by the generator and the pulses delivered to the target to be sampled and monitored.

Numerous other advantages and features of the present invention will become readily apparent from the following detailed description of the invention, from the claims and from the accompanying drawings.

BRIEF DESCRIPTION OF THE DRAWINGS

In the accompanying drawings that form part of this specification, and in which like numerals are employed to designate like parts in the same.

FIGS. 2A–2E are a set of simplified charts showing the pumping, generation, pulse feedback, energy feedback, and target thermal effects of a prior art laser device operating as a function of time, where only a single pulse of laser energy is generated in each pulse grouping;

FIGS. 3A–3E are a set of simplified charts showing the pumping, generation, pulse feedback, energy feedback, and target thermal effects of a laser device operating as a function of time and in accordance with the present invention, where two pulses of approximately equivalent energy and peak power are generated in each pulse grouping;

FIGS. 6A–6E are another set of simplified charts showing the pumping, generation, pulse feedback, energy feedback, and target thermal effects of a laser device operating as a function of time and in accordance with the present invention, where two pulses of differing energies and peak powers are generated in each pulse grouping.

DESCRIPTION OF THE PREFERRED EMBODIMENTS

Figure 1:
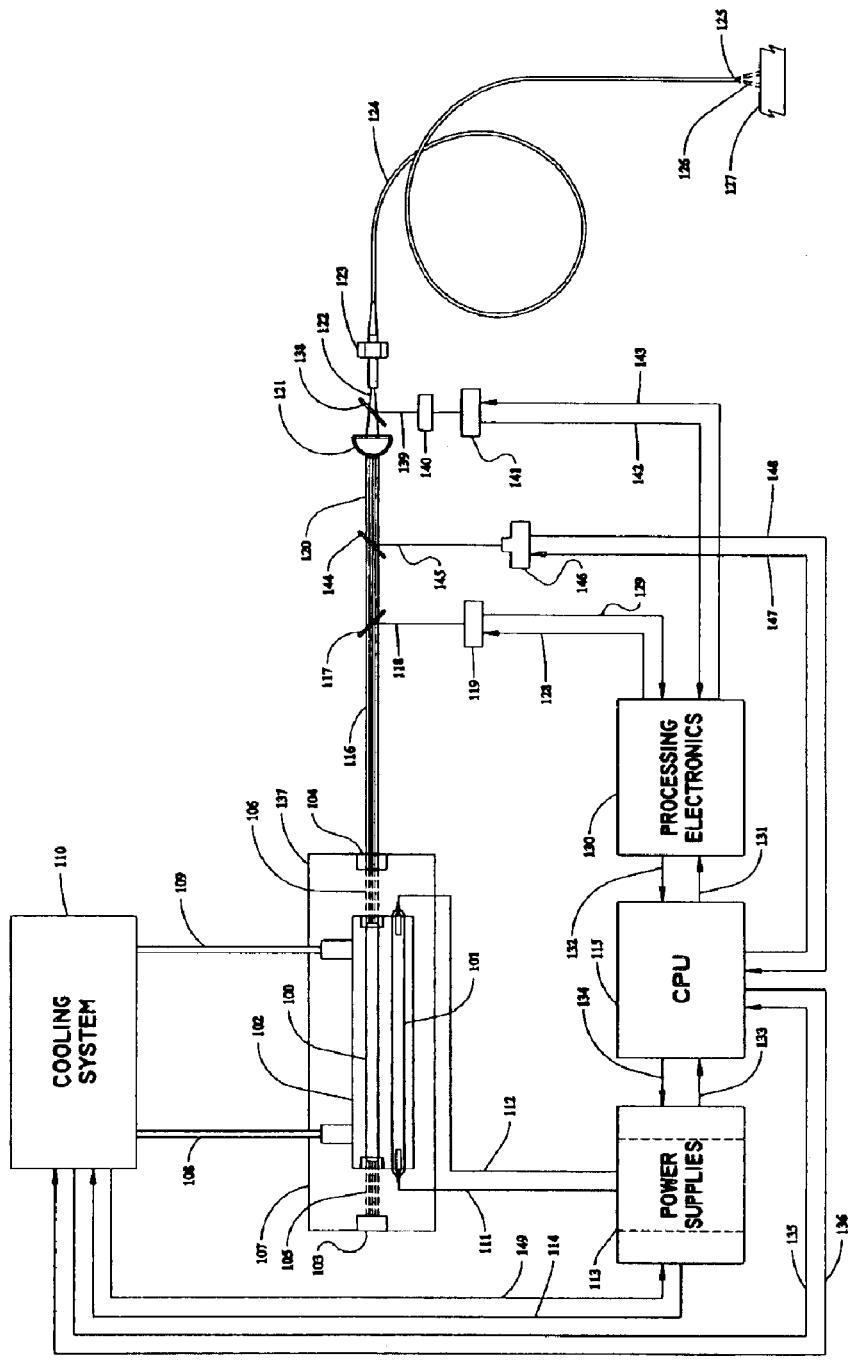
FIG. 1 is a schematic diagram of a water-cooled, flash lamp-pumped laser assembly coupled to a flexible optical fiber in accordance with one embodiment of the present invention.

The present invention provides an improved laser system and method for the generation and application of laser pulse trains using selected solid-state lasing media that is especially suitable for use in surgery and other medical, veterinary, industrial, and scientific applications. Existing laser systems may utilize multiple laser resonators, oscillators, or fiber amplifiers combined into one or more output beams, using means previously disclosed in the art, such as described in co-owned U.S. Pat. No. 5,387,211 to Saadatmanesh, et al.

The present invention enables essentially the same effect as described in U.S. Pat. No. 5,387,211 to be accomplished with only one laser resonator, oscillator, or fiber amplifier and one output beam, although the present invention may be used in combination with the invention described in the aforementioned U.S. Pat. No. 5,387,211. The laser system can efficiently generate and deliver multiple laser pulses in a pulse grouping within a relatively short time period, allowing substantially less input power to be used to generate substantially greater target effects.

While this invention is susceptible of embodiments in many different forms, this specification and the accompanying drawings disclose only some specific forms as examples of the invention. The invention is not intended to be limited to the embodiments or methods so described, however. The scope of the invention is pointed out in the appended claims.

For ease of description, the laser incorporating this invention is described in a selected operating position, and terms such as upper, lower, horizontal, etc., are used with reference to this position. It will be understood, however, that the laser incorporating this invention may be manufactured, stored, transported, used, and/or sold in an orientation other than those described.

Some of the figures illustrating embodiments of the apparatus show structural details and mechanical elements that will be recognized by one skilled in the art. However, the detailed descriptions of such elements are not necessary to an understanding of the invention, and accordingly are not presented herein.

Further, the apparatus incorporating this invention may be used with or contain certain conventional components, the details of which are not fully illustrated or described in detail except where a comprehension of their operation is useful in understanding the present invention. For example, this invention may be employed with one or more suitable conventional beam combination methods, mirrors, wave-guides and coupling systems, the details of which, although not fully illustrated or fully described, will be apparent to those having skill in the art and an understanding of the necessary functions of such components. The detailed descriptions of such components are not necessary to an understanding of the invention and are not herein presented because the constructional and operational details of such components per se form no part of the present invention.

The design, construction, and operation of various other components, including cooling systems, thermoelectric coolers, thermoelectric controllers, power supplies, flash lamps, arc lamps, laser diodes, hollow flexible wave-guides, partial and fully reflecting mirrors, adjustable mounts, and partial beam splitters are well known in the art. A few examples of such components are described in detail herein to exemplify how they may be employed in conjunction with the present invention. The details of the design, construction, and operation of these components per se form no part of the present invention.

The terms "laser energy", "laser radiation", "laser beam", and variants thereof used herein will be understood to encompass pulsed wave laser energy having a broad range of wavelengths, pulse widths, energy densities or fluxes, powers and repetition rate characteristics. A conventional laser resonator or oscillator utilizing one or more lasing ions in a solid-state host material, the combination of which have the characteristics of relatively long emission and energy storage lifetimes, may suitably produce laser radiation as part of the present invention. Examples of some selected lasing mediums that have these characteristics and can produce energies suitable for veterinary, medical, scientific and industrial applications include the following: Er:YAG, Tm:YAG, Ho:YAG, Er:YLF, Tm:YLF, Ho:YLF, Er:YSGG, Tm:YSGG, TmHo:YAG, CrTmHo:YAG, ruby and the like.

In general, solid-state lasing media may be pumped to population inversion to allow for efficient energy extraction and subsequent laser emission by a number of pumping means, for example, one or more flash lamp(s), laser diode(s), light-emitting diode(s), other laser(s) or other optical source(s), which are powered at substantially the same time. Extraction of the energy in the lasing medium may occur through several methods that are well known, including Q-switching, mode-locking, and free-running pulse extraction. For those solid-state lasing media that have relatively long emission and energy storage lifetimes, a significant amount of energy remains stored in the active medium after the end of each pulse of laser energy, when population inversion ceases to exist. Normally, this energy would be wasted in sub-threshold radiative and non-radiative decay prior to the next pump pulse in a repetitively pulsed system. However, in a system with a solid-state lasing medium that has relatively long emission and energy storage lifetimes, if the next optical pump pulse occurs sufficiently close in time to the end of the previous laser pulse, much of that stored energy can be utilized in the generation of the next pulse of laser energy and thus significantly less pump energy would be required to achieve population inversion. The efficiency of an optical system is typically measured as the ratio of the output power to the input power. Consequently, a system that takes advantage of this phenomenon will achieve higher efficiencies than a system that does not, which is described herein as part of the present invention.

A first type of laser device or system embodying the present invention is illustrated in FIG. 1. The device is suitable for generating and delivering pulses of laser radiation along a single beam path denoted by beam 116 either directly to a target site 127 (not illustrated), or through one or more types of conventional laser delivery systems, for example, the flexible optical fiber 124 depicted in FIG. 1. The system is particularly suitable for generating and delivering laser radiation to a target 127 of human or animal tissue on the surface of a body, within a natural lumen or cavity, or in a surgically created area, cavity, or passage in tissue. Typically, in medical or veterinary applications, the tissue at which the laser energy is directed may be characterized as a body site containing a material that is to be altered by the application of laser radiant energy. The material of target 127 may be part of the tissue per se or may be an altered form of tissue, such as cancerous tissue or atherosclerotic plaque. The material could also be an additional deposit on tissue, or matter to be removed or modified for industrial or scientific purposes.

The laser oscillator 107 shown in FIG. 1 is arranged and controlled, in conjunction with other components, to generate and deliver a pulse grouping of either a series of uniformly spaced pulses or a grouping of two or more pulses temporally close together that are repeated at regular intervals, i.e., as a pulse train. Such a grouping of pulses enables substantially less input power to be used and generates substantially greater target effects than a pulse train consisting of single pulses repeated at uniformly spaced intervals, as further explained later. In this embodiment, the laser oscillator 107 consists of multiple components that allow the efficient generation of the above-mentioned pulse train of pulse groupings that is part of the present invention. The laser oscillator 107 includes a solid-state lasing medium 100, containing one or more lasing ions doped in various concentrations within a host material that in combination have the characteristics of relatively long emission and energy storage lifetimes, and a flash lamp 101 for optically exciting the solid-state lasing medium 100 to achieve population inversion.

The solid-state laser oscillator also includes a pump chamber 102 that houses both the solid-state lasing medium 100 and flash lamp 101, that allows the efficient cooling of both the solid-state lasing medium 100 and the flash lamp 101, and that furthermore allows optical radiation transfer from the flash lamp 101 to the solid-state lasing medium 100. The laser oscillator 107 additionally has a support structure 137, upon which is mounted the pump chamber 102, a fully reflective optic in an adjustable mount 103, and a partially reflective optic in an adjustable mount 104. Both the fully reflective optic 103 and the partially reflective optic 104 are typically adjusted with their corresponding mounts to be centered on the beam paths 105 and 106 that go through the solid-state lasing medium 100.

In this embodiment of the present invention, the laser oscillator 107 is optically pumped and thermally managed using various support components. The pump chamber 102 that is part of laser oscillator 107 is thermally managed through a recirculating coolant loop that includes cooling system 110, pump chamber 102, and connections 108 and 109. Although denoted in FIG. 1 as cooling system 110, this subsystem may provide thermal stability below, at, or above room temperature, and may also provide heating to pump chamber 102. The solid-state lasing medium 100 in pump chamber 102 is optically pumped by flash lamp 101, which is powered by power supplies 113 through electrical connections 111 and 112. In this embodiment, the power supplies 113 also provide power to the cooling system 110 through connections 114 and 149, although this is not a necessary part of the laser device and method that incorporates the present invention. Both the optical pumping and cooling parameters in this embodiment may be controlled through a central processing unit (CPU) 115, through connection 134 to the power supplies 113 and connection 136 to the cooling system 110. The CPU 115 may have of one or more control system components, as known in the art. Both the power supplies 113 and the cooling system 110 subsystems may give feedback to the CPU 115 through connections 133 and 135, respectively, to inform the CPU 115 of their status and to facilitate system control.

During the operation of the laser oscillator 107, a process is initiated whereby a pulse of laser energy is generated and subsequently emitted along the axis denoted by beam 116. In the embodiment described in FIG. 1, the CPU 115 commands the power supplies 113 through connection 134 to provide a waveform of a commanded amplitude and pulse duration to the flash lamp 101 through electrical connections 111 and 112. In turn, the optical energy generated by flash lamp 101 is coupled both directly into the solid-state lasing medium 100 and indirectly into the solid-state lasing medium 100 through reflections off of the interior surfaces of pump chamber 102. As population inversion is achieved in solid-state lasing medium 100, one or more wavelength(s) of optical radiation pass multiple times through the solid-state lasing medium 100, as the optical radiation travels along beam paths 105 and 106 and are reflected off of both a fully reflective optic in an adjustable mount 103 and a partially reflective optic in an adjustable mount 104. Both the fully reflective optic 103 and the partially reflective optic 104 may be made up of one or more physical optics, comprised of various physical shapes and coated for the reflection and/or transmittance of various wavelength(s).

When a pulse of laser radiation is generated by laser oscillator 107 and emitted along the axis denoted by beam 116, part of the optical radiation generated by laser oscillator 107 may be sampled to facilitate monitoring and/or control of the present or future laser pulses. This is demonstrated in the embodiment of FIG. 1 through the use of a partial beam splitter 117, which redirects a portion of the energy in beam 116 along the path indicated by beam 118. Beam 118, which contains a percentage of the energy in the full beam 116, is then detected by one or more optical detectors 119, which convert the laser radiation in the wavelength(s) generated by laser oscillator 107 into other forms of electromagnetic radiation. These other forms of electromagnetic radiation, for example, other wavelengths of light, electrical signals, magnetic fields, microwaves, x-rays, and others, have frequencies, amplitudes and/or timing that are proportional to beam 118 and have the useful property that they are more easily processed by conventional components.

The optical detectors 119 provide signals that are proportional to the detected laser beam 118 to the processing electronics 130 through connections 128 and 129. The processing electronics 130 convert the electromagnetic radiation from optical detectors 119 into electrical form if necessary, and may also provide power to the optical detectors 119 through connections 128 and 129. Furthermore, the processing electronics condition the electrical signals from the optical detectors 119 into more useful forms for monitoring and/or control of the present and future pulses of laser radiation, the properties of such useful forms may be controlled by CPU 115 through connection 131. Once processed into useful forms by the processing electronics 130, the signals from optical detectors 119 are transmitted to the CPU 115 through connection 132. Subsequently, the CPU 115 may use this information to monitor the operation of the laser oscillator 107, the cooling system 110, the power supplies 113, the partial beam splitter 117, the optical detectors 119, the processing electronics 130, and each of the appropriate interconnections between these components and CPU 115. The CPU 115 may also use this information to control the outputs of the power supplies 113, cooling system 110, and processing electronics 130 in order to adjust the wavelength(s), amplitude, timing, total energy, and other parameters of the present and/or future laser pulses.

When a pulse of laser radiation is emitted along the axis denoted by beam 116, the part of the optical radiation from beam 116 that is not redirected by partial beam splitter 117 to beam 118 is directed along the axis denoted by beam 120 to the target 127. This direction of the beam 120 to the target 127 may be direct (not illustrated), may be through one or more optical elements (not illustrated), or may be through a flexible optical fiber 124 as depicted in FIG. 1. In this particular embodiment, beam 120 is directed through one or more optical elements 121 to condition the subsequent outgoing beam 122 for entrance into the proximal end 123 of a flexible optical fiber 124 of a given size and numerical aperture, suitable for transmittance of the wavelength(s) generated by laser oscillator 107. This flexible optical fiber 124 may be of a fixed or variable size and/or numerical aperture. The laser energy is then transmitted through flexible optical fiber 124 to the distal end 125 of flexible optical fiber 124. The distal end 125 of the flexible optical fiber 124 may be in contact with target 127 (not illustrated), may include one or more optical elements (not illustrated), or may be some distance away from target 127 as exemplified in FIG. 1. If the distal end 125 of flexible optical fiber 124 is in direct contact with target 127 (not illustrated), the optical beam 126 exiting the distal end 125 of flexible optical fiber 124 will be directly transmitted to the target 127. However, if the distal end 125 of flexible optical fiber 124 is not in direct contact with target 127, the optical beam 126 exiting the distal end 125 of flexible optical fiber 124 will be transmitted to the target 127 through a gaseous, fluid, or solid medium, one of which may be preferred to achieve the desired effects on target 127.

Subsequently, the effects on the target 127 of FIG. 1 may be monitored and the various parameters of optical beam 126 incident on the target may be controlled using a feedback mechanism, as known in the art, by feedback of reflective radiation from the target through the flexible optical fiber 124. As known in the art, the wavelength(s) emitted back from the target 127 being irradiated with optical beam 126 are typically different than the wavelength(s) generated by laser oscillator 107, and thus are separated from outgoing beam 122 by optic 138 after traveling back from target 127 through flexible optical fiber 124. Optic 138, which may be comprised of one or more optical elements, is optically coated to transmit the wavelength(s) generated by the laser oscillator 107 and to reflect the wavelength(s) emitted from the target 127.

The feedback wavelength(s) emitted from target 127 are then directed along beam path 139, through one or more conditioning optics 140, and then detected by one or more optical detectors 141. As these one or more optical detectors 141, along with their connections 142 and 143 to processing electronics 130, operate in a manner similar to one or more optical detectors 119 and connections 128 and 129, their operation is not again described in detail. The CPU 115 may use the information from one or more optical detectors 141 to monitor the effects of the laser radiation on target 127, and to control the outputs of the power supplies 113, cooling system 110, and processing electronics 130 in order to adjust the wavelength(s), amplitude, timing, total energy, and other parameters of the present and future laser pulses to produce the desired effects on the target 127.

A visible aiming beam may also be provided if desired. To this end, a low power semiconductor diode laser, helium-neon (HeNe) laser, or other visible light source 146 may be provided that directs a beam of light 145 to a beam combining mirror 144 which combines the wavelength(s) generated by laser oscillator 107 and the wavelength(s) of the aiming beam source 146 into a common beam path 120, as known in the art. The detailed design, construction, and operation of such an aiming beam source forms no part of the present invention.

Figure 4:
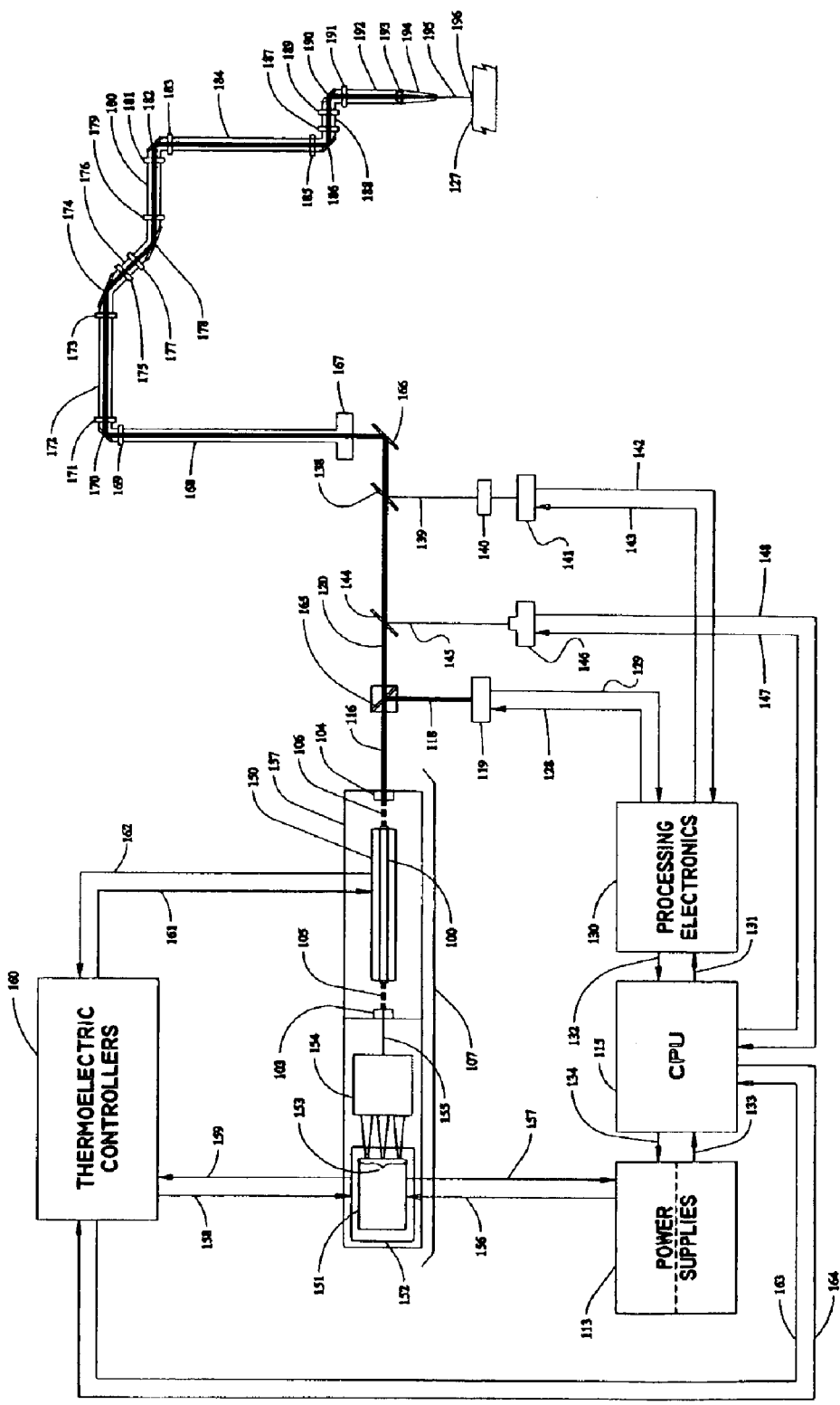
FIG. 4 is a schematic diagram of a thermoelectrically cooled, end diode-pumped laser assembly coupled to an articulated arm as another embodiment of the present invention.
Figure 5:
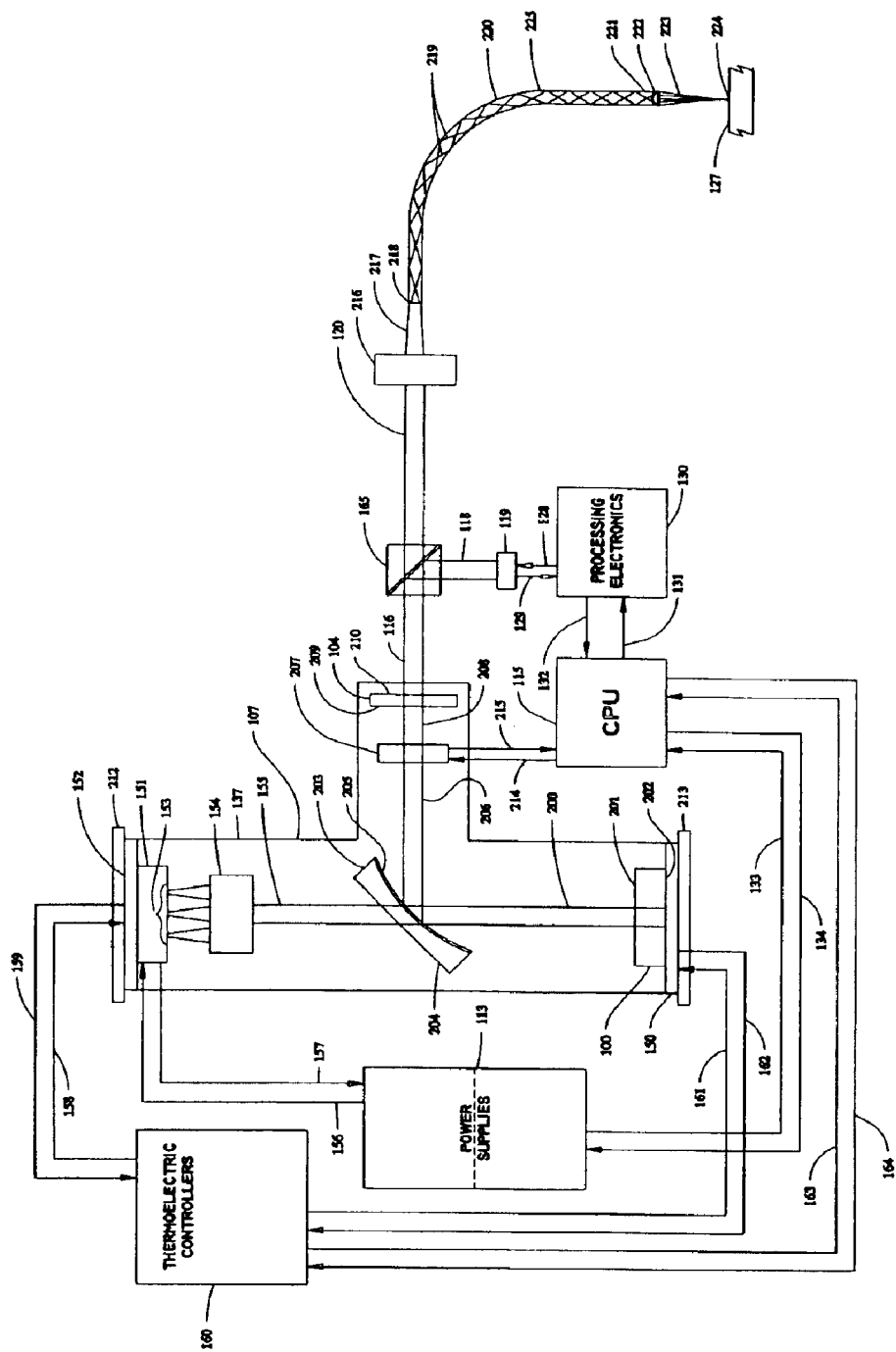
FIG. 5 is a schematic diagram of a thermoelectrically cooled, Q-switched diode-pumped laser assembly coupled to a flexible, hollow wave-guide as yet another embodiment of the present invention.

The embodiments expressed in FIGS. 1, 4, and 5 may include additional components, such as mirrors, coatings, focusing elements, beam divergence controlling optics, housings, programmable user interfaces, beam blocking devices or shutters, polarizing optics, Q-switching or mode-locking elements, and the like that are not illustrated. The detailed design and construction of such components per se form no part of the present invention.

It will also be appreciated that modifications may be made to the system illustrated in FIG. 1. The embodiment illustrated in FIG. 1 may also be adapted to pump a fiber amplifier to generate and deliver a pulse train with a grouping of two or more pulses within a short period of time that are repeated at regular intervals. In this alternate view of the embodiment of FIG. 1, the laser oscillator 107, cooling system 110, power supplies 113, CPU 115, output beam 116, partial beam splitter 117, optical detectors 119, and processing electronics 130 are employed to produce pulses of optical radiation for the purpose of pumping an optical fiber amplifier 124, doped with one or more lasing ions in various concentrations that have the characteristics of relatively long emission and energy storage lifetimes. The beam 120 is directed through one or more optical elements 121 to condition beam 122 for entrance into the proximal end 123 of an optical fiber amplifier 124 of a given size and numerical aperture, suitable for being sensitized with, being optically pumped or excited, and hosting one or more lasing ion(s). The output of the distal end 125 of the optical fiber amplifier 124 would then be delivered to the target 127 as previously described.

The target feedback mechanism described above, comprised of elements 138 through 143, may also be used in conjunction with the optical fiber amplifier 124 in the alternate view of the embodiment of FIG. 1. Furthermore, the target feedback mechanism along with the control system may also be modified to directly control the wavelength (s), amplitude, timing, total energy, and other parameters of the present and future laser pulses emitted from the optical fiber amplifier 124. This feedback mechanism is desirable to provide precise control of the radiant laser energy pulses generated in conjunction with the present invention.

A set of simplified charts showing the pumping, generation, pulse feedback, energy feedback, and target thermal effects of the operation of a typical pulsed laser system as a function of time are shown in FIGS. 2A–2E. These FIGS. 2A–2E illustrate the present art, in contrast to the generation of pulse trains consisting of pulse groupings shown in FIGS. 3A–3E, 6A–6E, and 7A–7E that are part of the method of the present invention.

As previously expressed, the waveforms in FIGS. 2A–2E include the optical pumping pulse waveform 251 of FIG. 2A, the output laser pulse waveform 252 of FIG. 2B, the laser pulse feedback waveform 253 of FIG. 2C that is proportional to the shape and timing of the laser pulse delivered in FIG. 2B, the laser energy feedback waveform 254 of FIG. 2D that is proportional to the energy of the delivered laser pulse in FIG. 2B, and the target thermal waveform 255 of FIG. 2E.

FIG. 2A illustrates optical pumping pulse waveform 251, consisting of repetitive, evenly spaced individual pulses. The shape of the leading and trailing edges of the optical pump pulses 256 and 265 and the amplitude of optical pumping pulses 257 and 266 are shown as being vertical and horizontal lines, respectively, although they may be some other wave shape that would preferentially shape the output laser pulse waveform 252 of FIG. 2B as desired. The individual optical pump pulses are separated by equivalent intervals, denoted by pulse waveform segments 261 and 270 of FIG. 2A. The delivery of an optical pumping waveform 251 of FIG. 2A to a laser oscillator allows the generation of an output laser pulse waveform 252 as shown in FIG. 2B.

FIG. 2C details a laser pulse feedback waveform 253 that is proportional to the shape and timing of the laser pulses delivered in FIG. 2B. As can be observed through a comparison of FIGS. 2B and 2C, the detected laser pulses 280 and 283, along with the spacing between pulses 263 and 272, are proportional in shape and timing to both the actual laser pulses 274 and 277 and the spacing between pulses 262 and 271 emitted from a laser oscillator.

FIG. 2D details an alternate laser energy feedback waveform 254 that is an integration of the laser pulse feedback waveform 253 of FIG. 2C, which may be of the wave shape shown or some other wave shape that is proportional to the energy contained within the individual laser pulses of the output laser pulse waveform 252 of FIG. 2B. The wave shape shown in FIG. 2D consists of rising edges 286 and 293, plateaus 287 and 294, falling edges 288 and 295, and spacing between pulses 264 and 273. Either the laser pulse feedback waveform 253 of FIG. 2C or the laser energy feedback waveform 254 of FIG. 2D, or both, may be used by a control system to monitor and control various parameters of the individual laser pulses of FIG. 2B, for example, amplitude, peak power, pulse width, pulse shape, and pulse energy. This allows each laser pulse to be controlled to nearly the same shape, timing, energy, and peak power, if desired.

FIG. 2E contains a target thermal waveform 255 showing the effects of the output laser pulse waveform 252 of FIG. 2B on target 127. This target thermal waveform 255 shows the temperature rises 300 and 307 on the surface of the target 127 above the target's normal temperature due to the delivery of laser pulses 274 and 277, respectively. The temperature of the target near the site of laser pulse delivery rises as laser pulses 274 and 277 start to be delivered and reaches thermal peaks 301 and 308 after the end of the delivery of the laser pulses 274 and 277, respectively. The reason for the delay between the end of laser pulses 274 and 277 and the thermal peaks 301 and 308 of the target 127 is due to the target thermal diffusion time constant. If this time constant is long, as is the case for many materials, for example, tissue, hair, cotton, wood, and the like, the delay between the end of the laser pulses 274 and 277 and the thermal peaks 301 and 308 of the target 127 is substantial. This time period, for example, can be on the order of a few hundred microseconds to a few milliseconds or longer. After the target temperature reaches peaks 301 and 308, it starts to cool back down to the target's ambient temperature. This is shown by decays 302 and 309 of the thermal peaks 301 and 308, respectively, and by the target's ambient temperature being achieved in target thermal waveform segments 255 and 306 of FIG. 2E. The above description summarizes the repetitive, evenly spaced individual laser pulses, and the effect on a target that they have, that is part of the present art as shown in FIGS. 2A–2E.

Another set of simplified charts showing the pumping, generation, pulse feedback, energy feedback, and target thermal effects of the operation of an embodiment of the method of the present invention as a function of time, where two pulses of approximately equivalent energy and peak power are generated in each pulse grouping of a pulse train, is shown in FIGS. 3A–3E. Again, as previously indicated, the waveforms in FIGS. 3A–3E include the optical pumping pulse waveform 251 of FIG. 3A, the output laser pulse waveform 252 of FIG. 3B, a laser pulse feedback waveform 253 of FIG. 3C that is proportional to the shape and timing of the laser pulse delivered in FIG. 3B, a laser energy feedback waveform 254 of FIG. 3D that is proportional to the energy of the delivered laser pulse in FIG. 3B, and the target thermal waveform 255 of FIG. 3E.

In the embodiments of the present invention, CPU 115 is used to control the shape and timing of the optical pumping pulse waveform 251 of FIG. 3A, typically through use of the feedback mechanism, comprised of elements 117 through 119 and 128 through 132, as described above. FIG. 3A illustrates the shape of the leading and trailing edges of the first 256 and second 260 optical pump pulses as vertical lines, and the amplitude and duration of both the first 257 and second 259 optical pumping pulses are shown as horizontal lines, although CPU 115 could control the shapes of these pulse waveform segments to be some other wave shape that would preferentially shape the output laser pulse waveform 252 of FIG. 3B as desired. The CPU 115 also controls the time interval between optical pumping pulses 258, which should be relatively short to allow the efficient generation of multiple pulses within a pulse grouping and can be of a fixed or variable duration, and the interval of time between groups of optical pumping pulses 261, which also can be of a fixed or variable duration.

Although FIG. 3A shows the optical pumping pulse waveform 251 as discrete pulses, other methods of optically pumping solid-state lasing medium 100 exist that allow the production of laser pulses. For example, the generation of laser pulses by continuous-wave pumping of a solid-state lasing medium 100 by a semiconductor laser diode source and Q-switching the output is also contemplated and may be used in conjunction with the present invention. In this example, the amplitude of the continuous-wave pumping between Q-switched output pulses may be adjusted, in addition to the timing and duration of the Q-switched output. The various methods, known in the art, of optically pumping a solid-state lasing medium may be used to allow the efficient generation and delivery of laser pulse groupings within a pulse train that are part of the present invention.

In FIG. 3A, the amplitude and duration of the second optical pump pulse 259 are shown as being lower and shorter than the amplitude and duration of the first optical pump pulse 257 to achieve output laser pulses of the same pulse energy. This is due to the fact that the solid-state lasing medium 100, within the laser oscillator 107, contains one or more lasing ions doped in various concentrations within a host material that have in combination the characteristics of relatively long emission and energy storage lifetimes, which can store optical energy in the interval between optical pumping pulses 258 as previously described. The amount of optical energy stored in the solid-state lasing medium 100 that is available to allow for more efficient optical pumping during the generation of subsequent pulses in the pulse grouping is dependent upon many factors. These factors include, for example, the shape of the leading and trailing edges of the first and second optical pumping pulses 256 and 260; the amplitude and duration of the first and second pumping pulses 257 and 259; the time interval between the optical pumping pulses 258; the time interval between groups of optical pumping pulses 261; the design, construction and operation of the laser oscillator 107; the design, construction, and operation of both the fully reflecting mirror 103 and partially reflecting mirror 104; the temperature of the solid-state lasing medium 100; the thermal stresses within the solid-state lasing medium 100; and the thermal lensing within the solid-state lasing medium 100.

With some combinations of the above factors in a given solid-state lasing medium, an order of magnitude or greater reduction in the subsequent pump pulse energy in comparison with the first pump pulse energy is possible to achieve output pulses of the same amplitude and pulse width. For example, operation of the laser oscillator 107 at low output pulse energies, repetition rates near the low end of the design margin of the laser oscillator, and little time between pulses can produce pulse groupings with these characteristics.

Particularly, in a pulsed, flash lamp pumped system using a CrTmHo:YAG lasing medium at room temperature, there are at least five transitions required in order to lase at 2,100 nm, in addition to upconversion transitions in both thulium and holmium in this medium. Many of the non-ground states in this medium can store significant energy after the end of a laser pulse when radiative emission at 2,100 nm has gone below the lasing threshold. If an additional optical pump pulse is introduced within a relatively short time interval, for instance, about 1 ms, after the end of the first laser pulse, the input energy required for this pump pulse to allow the same output energy from the second laser pulse as was present in the first laser pulse is substantially reduced. The second pump pulse energy, in this example of one of the preferred embodiments, has been measured to be as low as an order of magnitude less than the first pump pulse energy to achieve output pulses of the same energy level.

With other combinations of the above factors in the same solid-state lasing medium, the subsequent pump pulse energy required to realize output pulses of the same amplitude and pulse width may be greater than the first pump pulse energy. For example, operation of the laser oscillator 107 at high output pulse energies, repetition rates near the high end of the design margin of the laser oscillator, at average powers near or above the design margin of the laser oscillator, and with greater time intervals between pulses can produce pulse groupings with these characteristics. Regardless of other factors, if the time between pulses in a pulse grouping is long, for example, much longer than the emission and energy storage lifetimes of the solid-state lasing medium employed, the energy remaining in the medium after the end of each pulse of laser energy is wasted in sub-threshold radiative and non-radiative decay prior to the next optical pump pulse. Thus, in this example, beneficial use of this energy is not possible and the efficiency of the laser oscillator reverts to that normally experienced in typical repetitively pulsed laser systems. Other practical factors that can strongly increase the energy needed in the second optical pumping pulse include, for example, sub-optimal thermal stress management and sub-optimal thermal lensing management in the design, operation, and construction of the laser oscillator.

Although both the amplitude and duration of the second optical pump pulse 259 are shown in FIG. 3A as lower than the amplitude and duration of the first optical pump pulse 257, it is also possible under other conditions that these characteristics of the second or subsequent optical pump pulse 259 may be higher than those of the corresponding first optical pump pulse 257 to generate laser pulses that contain the same energy per pulse. The efficient generation of laser pulses, as described in this specification, is present when the efficiency (i.e. output energy/input energy) of the second or subsequent optical pump pulse 259 is higher than the efficiency of the first optical pump pulse 257, and is not present when these conditions are not fulfilled. However, operation of an embodiment utilizing the present invention is possible under conditions where the efficient generation of laser pulses is not present in order to obtain a desired target effect with a pulse train consisting of pulse groupings. This is especially significant when the desired target effect may not be otherwise obtained using a combination of parameters during which the efficient generation of laser pulses is possible in a given implementation.

The second or subsequent pulses in a pulse grouping may contain higher, lower, or the same energy levels as the first pulse in the pulse grouping. Additionally, each pulse in the pulse grouping may be at the same or at different levels from the other individual pulse(s) in the pulse grouping. The efficient generation of laser pulses is also possible under these conditions, even if the second or subsequent pulses contain less energy than the first pulse in the pulse grouping. This is true as long as the efficiency of the second or subsequent pulse(s) is higher than the efficiency of a stand-alone pulse of the same energy.

FIG. 3B shows an output laser pulse waveform 252 that is generated by the delivery of an optical pumping waveform 251 of FIG. 3A to a laser oscillator 107. Both the first 274 and second 276 laser pulses in FIG. 3B are of approximately the same energy, pulse width, peak power, and shape, and are separated by a relatively short interval 275. This is a result of CPU 115 control of the various operational parameters that allow the efficient generation of nearly identical laser pulses in a pulse grouping.

The operational parameters that are controlled in order to allow the efficient generation of laser pulse groupings may include, for example, the amplitude, duration, and shape of the first and subsequent optical pump pulses in the pulse grouping, as shown by elements 256 through 260; the time interval between pulses in the grouping 258; the time interval between the groupings of laser pulses 261; and the temperature of the solid-state lasing medium 100. The time interval between groupings of laser pulses 262 is nearly identical to the time interval between groupings of optical pump pulses 261, which in general should be substantially longer than the time interval between laser pulses 275, depending upon the desired target effects.

FIG. 3C illustrates a laser pulse feedback waveform 253 that is proportional to the shape and timing of the laser pulses delivered in FIG. 3B. As can be observed through a comparison of FIGS. 3B and 3C, the first and second detected laser pulses 280 and 282, as detected by optical detector 119, are proportional in shape and timing to the actual first and second laser pulses 274 and 276 emitted from laser oscillator 107. Moreover, the detected time interval between both the individual laser pulses 281 and the laser pulse groupings 263 are almost identical to the actual time interval between both the individual laser pulses 275 and laser pulse groupings 262. This detected laser pulse feedback waveform 253, after going through the processing electronics 130, is used by CPU 115 to determine and control various parameters of the first and second laser pulses of the pulse grouping, for example, amplitude, peak power, pulse width, pulse shape, pulse energy, and the time interval between pulses.

FIG. 3D shows a laser energy feedback waveform 254 that is proportional to the energy of the individual laser pulses in FIG. 3B, which may alternately be used by CPU 115 to determine the energy contained within the each of the laser pulses in the pulse grouping. In the operation of this embodiment, the processing electronics 130 would perform an integration of the laser pulse feedback waveform 253 in order to determine the energy delivered by the first 274 and second 276 laser pulses in the pulse grouping.

In FIG. 3D, rising edge 286 is an integration of the first detected laser pulse 280 of the pulse grouping, performed by an integrating operational amplifier or other similar conventional circuit (not illustrated). The integrated waveform is then sampled by a sample-and-hold circuit (not illustrated), as is commonly known and utilized in the art. The sample-and-hold circuit thus holds the plateau or flat portion 287 of this waveform at the same level as the peak of the rising edge 286, which is proportional to the energy delivered by the first pulse 274 of laser oscillator 107. This plateau 287 may then be sampled through the use of an analog-to-digital converter (not illustrated) or other conventional means and used by the CPU 115 to determine the actual laser energy delivered by the first pulse 274 of laser oscillator 107. After the CPU 115 samples the flat portion 287 of laser energy feedback waveform 254, which occurs preferably in the time interval between laser pulses 275, the CPU would then send a command to the processing electronics 130 through connection 131 to zero out both the integrator and sample-and-hold circuits to prepare them to measure the energy within the next laser pulse in the pulse grouping. This is shown in waveform 254 by the removal of the accumulated charge in the integrator and the value held by the sample-and-hold circuit through falling edge 288 and a net zero charge in the integrator through trough 289 between laser pulses in the pulse grouping. For the second detected laser pulse 282 in the pulse grouping, the above process is repeated through rising edge 290, plateau 291, falling edge 292, and the interval between laser pulse groupings 264.

FIG. 3E details the target thermal waveform 255 showing the effects of the output laser pulse waveform 252 on target 127. This target thermal waveform 255 shows the temperature rise 300 on the surface of the target 127 due to the delivery of the first laser pulse 274 from laser oscillator 107. The temperature of the target near the site of laser pulse delivery starts rising as the first laser pulse 274 is starting to be delivered and reaches a peak 301 after the end of the delivery of the laser pulse 274. The reason for the delay between the end of the first laser pulse 274 and the first thermal peak 301 of the target 127 is due to the target thermal diffusion time constant. If this time constant is long, as is the case for many materials, for example, tissue, hair, cotton, wood, and the like, the delay between the end of the laser pulse 274 and the thermal peak 301 of the target is substantial. This time period, for example, can be on the order of a few hundred microseconds to a few milliseconds or longer.

After the target temperature reaches a peak 301, the target starts to cool back down to ambient temperature. This is shown by the decay 302 of the first thermal peak 301. If the delay between laser pulses 275 is sufficiently short, for example, a time period that is shorter than the target thermal diffusion time constant, the effect of the second laser pulse 276 in the pulse grouping will be a second temperature rise 303 that will start from a temperature that is close to the first thermal peak 301. The target temperature will then reach a second thermal peak 304 due to the second laser pulse 276, followed by a second decay 305 that returns the target surface temperature back down to the target's ambient temperature, assuming that the time between laser pulse groupings 262 is substantially longer than the target thermal diffusion time constant.

In this case in point, the temperature rise 301 of the first laser pulse 274 assists in allowing the second laser pulse 276 to impart an enhanced thermal effect through the second temperature rise 303 of the target 127. The net effect of the two pulse grouping in the target thermal waveform 255 is of a laser pulse of about twice the energy of the two individual laser pulses 274 and 276, without laser oscillator 107 having to generate a single pulse of about twice the energy per pulse. This has the numerous and apparent advantages of reducing laser oscillator 107 complexity, having lower optical damage thresholds for optical elements and coatings, lowering the chances of damaging laser delivery devices due to excessive fluence levels, and decreasing overall system size, complexity and cost. These advantages can be attained through the use of pulse groupings in a pulse train that are part of the present invention.

During the operation of an embodiment of the present invention shown in FIG. 3E, target temperature segment 306 in the target thermal waveform 255 is close to the ambient temperature of target 127 in a near steady state condition. Consequently, in this instance, both the interval between groupings of optical pump pulses 261 and the interval between groupings of laser pulses 262 are much longer than the thermal diffusion time constant of the target 127. For example, in medical applications involving various tissues, it is desirable to allow the tissue surrounding the laser application site to cool back to the tissue's ambient temperature between groups of pulses to help prevent collateral tissue damage due to localized overheating of the surrounding tissue. However, the period between groupings of laser pulses 262 do not have to be of this duration, especially if some elevation of the target temperature is useful in achieving the desired target effects. For example, in certain forms of industrial materials processing, the groupings of laser pulses may be applied in a series across the surface of a target material 127, where the localized heating from the previous groupings of pulses would allow the subsequent groupings of laser pulses to achieve the desired target effects with less total power or energy exposure than would otherwise be needed at a lower target temperature.

In FIG. 3A, when the CPU 115 has determined that the fixed or variable time between groupings of optical pumping pulses 261 and the corresponding interval between laser pulses 262 has elapsed, the CPU 115 will initiate the next grouping of optical pumping pulses as depicted by pump waveform segments 265 through 270. The information gathered from previous laser pulse groupings, including the information from FIGS. 3C and 3D, along with the optionally detected target thermal waveform 255 of FIG. 3E, may be used by CPU 115 to control the optical pumping pulse waveform 251 of FIG. 3A and consequently the output laser pulse waveform 252 of FIG. 3B for the present grouping of laser pulses. Thus, in this subsequent pulse grouping in FIG. 3A, the timing and shape of the rising and falling edges of the first and second optical pumping pulses 265 and 269, the amplitude and shape of the duration of the first and second optical pumping pulses 266 and 268, the interval between optical pumping pulses 267 and between pulse groupings 270 are all controlled by CPU 115 based upon the information from the above described waveforms for the present and previous pulse groupings. This allows the two pulses of the output laser pulse grouping in FIG. 3B to be controlled to be of nearly the same shape, timing, energy, and peak power.

The CPU 115 control of the second grouping of optical pumping pulses, denoted by pump waveform segments 265 through 270 of FIG. 3A, allows the generation of the second grouping of output laser pulses, denoted by pulse waveform segments 271 and 277 through 279 of FIG. 3B. The features and details of operation of the second grouping of laser pulses are similar to those of the first grouping of laser pulses and thus they are not described again in detail. This includes pump waveform segments 271 and 277 through 279 in FIG. 3B, pulse feedback waveform segments 272 and 283 through 285 in FIG. 3C, pulse energy feedback waveform segments 273 and 293 through 299 in FIG. 3D, and target thermal waveform segments 307 through 312 in FIG. 3E. These features are denoted for clarification that the pulse groupings of laser pulses may be employed in a repetitive manner, although it will be recognized that the present invention may also be employed with a single grouping of laser pulses.

The wavelength(s), amplitude, timing, total energy, and other parameters of the individual pulses in a pulse grouping can be utilized to modulate the various effects of the pulsed laser beam as described below.

In order to maximize the available acoustic effects of a pulsed laser beam, for example, for fragmenting a relatively hard material such as a urinary or biliary stone, the pulse spacing of laser pulses of a given wavelength is minimized, and the pulses subsequent to the first pulse may have an increased pulse width, amplitude, and/or energy. By spacing the consecutive pulses relatively close to one another, for example, before the acoustic shock wave of the first pulse subsides, the effective pulse width and energy delivered to the target 127 is substantially increased, thus enabling a relatively higher energy to be delivered to the target without damage to a laser delivery device used to transmit the same. This is particularly beneficial for the delivery of relatively high-energy pulses from short-pulsed, Q-switched, or mode-locked lasers.

Conversely, in order to minimize the acoustic effects of a pulsed laser beam, for example, for ablating a relatively hard material such as a urinary or biliary stone in a large, fluid-filled cavity and to prevent the acoustic effects of the laser pulses from being additive and propelling the stone away from the laser delivery device, or damaging the duct in which the stone is located or adjacent tissue, the individual pulses may be spaced such that the photo-acoustical shock wave of each pulse in the pulse grouping subsides prior to delivery of a subsequent pulse. For example, with a wavelength of 2100 nm, a pulse width of at least 100 microseconds, and a pulse energy of at least 100 mJ, the pulses would be spaced at least 800 microseconds apart.

In contrast, to maximize the thermal effects while minimizing the acoustic effects of a grouping of two or more laser pulses, the individual consecutive pulses would be spaced such that both the acoustic shock wave of a pulse would subside prior to the delivery of a subsequent pulse and that the pulses within the grouping are cascaded within a time period that is preferably shorter than the target thermal diffusion time constant. This interval between pulses would thus be within a time period that is less than the period during which the heat generated by the preceding pulse is substantially dissipated. The duration of this interval between pulses varies with the target's thermal diffusion time constant, which is a function of the type of target material 127, and the desired effect of the laser pulses on the target material. For example, when the target thermal diffusion time constant (k) is 150 milliseconds, utilization of the aforestated formula $$T_e = T_a + (T_s - T_a) e^{-t/k}$$

reveals that starting with a target temperature of 100 degrees C and an ambient temperature of 25_C, the target temperature after 8 milliseconds is $$T_e = 25 + (100-25) e^{-0.008/0.15} = 96.1 \text{ degrees C.}$$

Accordingly, the delivery of a second, third, fourth, etc. laser pulse within 8 milliseconds, in this example, from the delivery of the preceding pulse will cause an accumulation of their respective thermal effects on the target material 127, with the increase in target temperature starting from about the peak temperature from the first laser pulse.

The present invention permits the employment of commercially available laser generators that produce laser beam energies subject to significant attenuation during transmission. During one mode of operation of a repetitively pulsed, solid-state laser system, the laser oscillator 107 is operated to produce laser pulses that are spaced at equivalent time intervals from each other, for example, with a pulse energy of about 4 joules at the emission port so as to deliver about 3.2 joules to the target at a repetition rate of 15 Hz. During a mode of operation contemplated by the present invention of a repetitively pulsed, solid-state laser system, the laser oscillator 107 is operated to produce pulse groupings of pulses that occur during a relatively short time span that are spaced at equivalent fixed or variable time intervals from each other, for example, with a pulse energy of about 2 joules from the first and subsequent pulses in the pulse grouping at the emission port so as to deliver about 1.6 joules to the target at a pulse grouping repetition rate of 15 Hz.

As was previously described as part of the present invention, the laser pulses can more efficiently effect a target 127, such as tissue, if pulse groupings are used that have pulse spacings with both relatively short durations and that occur at equivalent fixed and/or variable time intervals from each other. For example, for laser pulses having a pulse width of about 300 microseconds and a fixed repetition rate of 15 Hertz, it would be desirable to initiate the second pulse in a pulse grouping within 0.10 to 10 milliseconds of the end of the first pulse of laser energy. By the appropriate control of the power supplies 113 that permit the generation of the optical pumping pulse waveform 251 by CPU 115, for example, pairs of consecutive laser pulses can be produced such that the interval between the two pulses is as small as a few picoseconds.

The delivery of successive individual laser pulses with a relatively short time interval between them has a similar effect in relation to the target site in a thermodynamic sense as if it were a single laser pulse having the combined energies of the plural pulses in the pulse grouping. From an acoustic sense, however, the delivered pulses in the pulse grouping can remain as two separate laser pulses inasmuch as an acoustic shock and its associated vapor or plasma bubble can dissipate within, for example, about 800 to 900 microseconds. That is, the emission of consecutive laser energy pulses within a pulse grouping can be controlled so that such pulses are emitted sufficiently close in time to one another to elicit an additive acoustic effect at a target site, for example, during the fragmentation of kidney or gall stones. Similarly, the emission of consecutive laser energy pulses within a pulse grouping can be controlled to elicit an additive thermal effect without eliciting an additive acoustic effect at a target site, for example, during the ablation of bone or tissue at a blood vessel obstruction.

The principles of the present invention can also be applied to other embodiments, including in systems employing a thermoelectrically cooled, end diode-pumped laser assembly coupled to an articulated arm laser delivery device. Thus, in contrast to FIG. 1, FIG. 4 reveals a system in which thermoelectric cooling replaces conventional liquid cooling; a semiconductor laser diode array end-pumps a solid-state lasing medium, replacing a flash lamp that side-pumps a solid-state lasing medium; and an articulated arm laser delivery device is used that replaces a flexible optical fiber delivery device.

In the embodiment illustrated in FIG. 4, the laser oscillator 107 consists of multiple components that permit the efficient generation of the above mentioned pulse groupings in accordance with the method of the present invention. Some of these components and their properties are similar to those shown in the embodiment of FIG. 1, such as the solid-state lasing medium 100, a fully reflective optic in an adjustable mount 103, and a partially reflective optic in an adjustable mount 104, and are not once again described in detail. The laser oscillator 107 of FIG. 4 also partially consists of other components, such as a lasing medium thermoelectric (TE) cooler 150 for housing the solid-state lasing medium 100 and facilitating efficient cooling of the same, and a semiconductor laser diode array 151, which contains one or more laser diodes for optically exciting and achieving population inversion in the solid-state lasing medium 100. This laser oscillator 107 also consists of a laser diode TE cooler 152 for housing the semiconductor laser diode array 151 and allowing efficient cooling of the same, and an array of optical elements 154, which contains one or more elements for combining and collimating the multiple laser beams 153 from the semiconductor laser diode array 151 into a single, substantially collimated beam 155. The laser oscillator 107 furthermore consists of a support structure 137, upon which is mounted the lasing medium TE cooler 150, the laser diode TE cooler 152, the array of optical elements 154, a fully reflective optic in an adjustable mount 103, and a partially reflective optic in an adjustable mount 104. The fully reflective optic 103, the partially reflective optic 104, and the array of optical elements 154 are typically adjusted with their corresponding mounts to be centered on the beam paths 155, 105, and 106 that go through the solid-state lasing medium 100.

The solid-state lasing medium 100 in laser oscillator 107 is optically end-pumped by semiconductor laser diode array 151, which is powered by power supplies 113 through electrical connections 156 and 157 as shown in FIG. 4. This semiconductor laser diode array 151 optically excites the solid-state lasing medium 100 to population inversion by emitting one or more pump laser beams 153 into an array of optical elements 154 for combining and collimating the multiple laser beams 153 into a single, substantially collimated beam 155 which then goes through the fully reflective optic 103 and beam path 105 to reach the solid-state lasing medium 100. In this embodiment, the optics 103 and 104 may be coated, as known in the art, to allow the optical pump beam to pass through the solid-state lasing medium 100 twice, in order to maximize the absorption of the pump wavelength(s) emitted from the semiconductor laser diode array 151 by the solid-state lasing medium 100.

As represented in FIG. 4, the laser oscillator 107 is thermally managed by utilizing an assortment of support components. Both the lasing medium TE cooler 150 and the laser diode TE cooler 152 thermally manage the solid-state lasing medium 100 and the semiconductor laser diode array 151, respectively, by removing excess heat from these components and spreading that excess heat to the support structure 137, which also acts as a heat sink for the laser oscillator 107. The cooling system of FIG. 4 is comprised of the lasing medium TE cooler 150, the lasing medium TE cooler connections 161 and 162, the laser diode TE cooler 152, the laser diode TE cooler connections 158 and 159, the support structure 137, and the thermoelectric (TE) controllers 160. The TE controllers 160 can provide thermal stability for the solid-state lasing medium 100 and the semiconductor laser diode array 151 below, at, or above room temperature, and at the same or different temperatures to allow lower power consumption and greater lasing efficiency. In this embodiment, the power supplies 113 also provide power to the TE controllers 160 through connections 133 and 134 to the CPU 115, along with connections 163 and 164 to the TE controllers 160.

The components of both the power supplies 113 and the TE controllers 160 may give feedback to facilitate CPU 115 control through connections 133 and 163, respectively, and their outputs may be controlled by way of the CPU 115, through connections 134 and 164 to the power supplies 113 and TE controllers 160, respectively.

During operation of the laser oscillator 107 of FIG. 4, a pulse of laser energy is generated and directed along the axis denoted by beam 116. The CPU 115 commands the power supplies 113 through connection 134 to provide a waveform of a commanded pulse amplitude and duration to the semiconductor laser diode array 151 through connections 156 and 157. In turn, the optical energy generated by the semiconductor laser diode array 151 is end-coupled into the solid-state lasing medium 100 through components 154 and 103, using beam paths 155 and 105 as previously described. When population inversion is achieved, the laser oscillator 107 operates as known in the art, emitting a portion of the optical radiation as the output laser beam 116. In an alternate approach to achieving beam 116, CPU 115 may command the power supplies 113 through connection 134 to provide a continuous supply output to the semiconductor laser diode array 151 through connections 156 and 157, which produces a continuous wave (CW) output from the semiconductor laser diode array 151. In this instance, an intra-cavity Q-switch (not illustrated) could be used to produce pulses of laser energy from the laser oscillator 107, with operation similar to the Q-switching elements 207 of FIG. 5.

When a pulse of laser radiation is generated by laser oscillator 107 of FIG. 4 and directed along the axis denoted by beam 116, part of the optical radiation may be sampled to facilitate monitoring and control of the present or future laser pulses, through the use of a prism beam splitter 165, which directs a portion of the energy from beam 116 along the path indicated by beam 118. The remainder of the pulse sampling components and operation, including components 119, 130, 115, 128, 129, 131 and 132 remain similar to those described in conjunction with FIG. 1 and are not once again expressed in detail. Subsequently, the CPU 115 may use the information from the sampled laser pulses to monitor the proper operation of components 107, 160, 113, 165, 119, 130, and each of the applicable interconnections between these components, and to control the outputs of components 113, 160, and 130 in order to adjust the wavelength(s), amplitude, timing, total energy, and other parameters of the present and future laser pulses.

After the laser oscillator 107 of FIG. 4 emits a beam 116 of laser radiation, the portion of the beam 116 that is not redirected by partial beam splitter 117 is directed along the axis indicated by beam 120 to the target 127. This direction may be through various means, including the redirection of beam 120 by mirror 166 into the proximal end of an articulated arm 167, which is of a given fixed or variable size and is suitable for transmittance of the wavelength(s) generated by laser oscillator 107. The construction and operation of articulated arm 167 is known in the art and consists of: segments 168, 172, 176, 180, 184, 188, and 192; rotating joints 169, 171, 173, 175, 177, 179, 181, 183, 185, 187, 189, and 191; adjustable mirrors 170, 174, 178, 182, 186, and 190; and handpiece 194 containing one or more optical elements 193. Beam 120 is directed along the interior of this articulating arm 167 by reflecting off of mirrors 170, 174, 178, 182, 186, and 190, and through one or more optical elements 193, until it exits the articulating arm 167 as beam 195. Beam 195 is directed to the target 127 by repositioning the articulated arm 167 through handpiece 194 until beam 195 strikes the target 127 at site 196.

Furthermore, the effects on the target 127 of FIG. 4 may be monitored and the various parameters of the beam 195 may be controlled to produce the desired results at target site 196 using a feedback mechanism, as known in the art, by processing reflective radiation from the target through the articulated arm 167. Such a feedback system may regulate the wavelength(s), amplitude, timing, total energy, and other parameters of the present and future laser pulses to produce these desired effects. As the components and operation of such a feedback system, including the monitoring and control of various outputs, expressed by elements 138, 139, 140, 141, 130, 115, 113, 160, 131, 132, 142, and 143, are similar to those described in conjunction with FIG. 1, they are not once again described in detail.

An aiming beam may also be provided if desired with the embodiment represented in FIG. 4. The components and operation of this aiming beam, including elements 146, 145, 144, 115, 147, and 148 remain the same as described in conjunction with FIG. 1 and are not once again described in detail.

FIG. 5 illustrates yet another embodiment of the present invention which employs a thermoelectrically cooled, Q-switched, diode-pumped laser assembly coupled to a flexible, hollow wave-guide beam delivery device. In contrast to FIG. 1, this embodiment uses thermoelectric cooling in place of conventional liquid cooling, a semiconductor laser diode array that end-pumps the solid-state lasing medium instead of a flash lamp that side-pumps the solid-state lasing medium, and a flexible, hollow wave guide delivery device in lieu of the flexible optical fiber delivery device. However, the operation of those embodiments depicted in FIGS. 4 and 5 are quite similar to one another, and thus only the differences between FIGS. 4 and 5 are detailed below.

In the embodiment represented by FIG. 5, the laser oscillator 107 consists of multiple components that allow the efficient generation of the above-mentioned pulse train of pulse groupings that are part of the method of the present invention. Some of these components and their properties are similar to those shown in the embodiment of FIG. 4, such as elements 100, 150, 151, 152, 154, and 104, and are thus not again described in detail. The laser oscillator 107 furthermore partially consists of a lasing medium TE cooler heat sink 213, upon which is mounted the solid-state lasing medium 100 and to which heat extracted from the same is directed, a laser diode TE cooler heat sink 212, upon which is mounted the semiconductor laser diode array 151 and to which heat extracted from the same is directed, and a support structure 137, upon which is mounted the lasing medium TE cooler heat sink 213, the laser diode TE cooler heat sink 212, the array of optical elements 154, the intra cavity redirecting optic 203, the Q-switching elements 207, and a partially reflective optic in an adjustable mount 104.

In the laser oscillator 107 of FIG. 5, the fully reflective optic is the rear surface 202 of the solid-state lasing medium 100, the partially reflective optic is front surface 209 of the partially reflective optic 104, and oscillator itself includes solid-state lasing medium 100, intra cavity redirecting optic 203, Q-switching elements 207, and partially reflective optic 104. Surface 205 of intra cavity redirecting optic 203 is curved to allow a large volume of the solid-state lasing medium 100 to be excited by the optical pumping beam and to collimate the oscillator output beam, which has the advantage of creating a small beam size at the Q-switching elements 207.

For proper operation of the laser oscillator 107, the array of optical elements 154 is typically adjusted with its corresponding mounts to be centered on the beam paths 155 and 200, the intra cavity redirecting optic 203 is typically adjusted with its corresponding mount to be centered on and at about a 45 degree angle to the beam path 200 to create beam path 206, and the Q-switching elements 207 and partially reflective optic 104 are typically adjusted with their corresponding mounts to be centered on the beam paths 206 and 208.

In FIG. 5, solid-state lasing medium 100 is optically pumped utilizing and going through elements 151, 113, 156, 157, 153, 154, 155, 203, and 200, in a manner similar to that shown in FIG. 4, and is thus not again described in detail. In this embodiment, any of the optics 100, 104, and 203 may be made up of one or more physical shapes or elements, and their surfaces 201, 202, 204, 205, 209, and 210 coated for the reflection and/or transmittance of various wavelength(s), to ensure their desired operation.

As indicated in FIG. 5, laser oscillator 107 is thermally managed using a variety of support components. However, since these components and their functions are similar to those illustrated in FIG. 4, including lasing medium TE cooler 150, lasing medium TE cooler heat sink 213, laser diode TE cooler 152, laser diode TE cooler heat sink 212, support structure 137, connections 161, 162, 158, 159, 133, 134, 163, 164, and the thermoelectric (TE) controllers 160, they are not again described in detail.

As was the case for FIG. 4, both the optical pumping and cooling parameters in FIG. 5 may be controlled by way of the CPU 115, through connections 134 and 164 to the power supplies 113 and TE controllers 160, respectively. The components of both the power supplies 113 and the TE controllers 160 may also give feedback to facilitate CPU 115 control through connections 133 and 163, respectively.

In the preferred embodiment of FIG. 5, the CPU 115 commands the power supplies 113 to provide a continuous supply output to the semiconductor laser diode array 151 through connections 156 and 157, which produces a continuous wave (CW) output from the semiconductor laser diode array 151. The one or more pump laser beams 153 from the semiconductor laser diode array 151 go through an array of optical elements 154 for combining and collimating the multiple pump laser beams 153 into a single, substantially collimated beam 155 which then passes through the intra cavity redirecting optic 203 and beam path 200 to reach the solid-state lasing medium 100. The optical pump energy travels a path through the solid-state lasing medium 100 that involves going through its front surface 201, its length, reflecting off of its back surface 202, and then going through its length again. In this manner, the optical pump beam can pass through the solid-state lasing medium 100 twice, in order to maximize the absorption of the pump wavelength(s) emitted from the semiconductor laser diode array 151 by the solid-state lasing medium 100.

During the operation of the laser oscillator 107 of FIG. 5, a process is initiated whereby a pulse of laser energy is generated and subsequently emitted. The active Q-switching elements 207 are commanded by the CPU 115 through connection 214 to not permit laser output while the solid-state lasing medium 100 is being optically pumped to achieve population inversion. In this instance, the active Q-switching elements 207 are also supplied power by the power supplies 113 through connections 133 and 134, the CPU 115, and connections 214 and 215. At the appropriate time, CPU 115 commands the active Q-switching elements 207 to permit one or more wavelength(s) of optical radiation to pass multiple times through the components of the laser oscillator 107. The optical radiation consequently reflects off of surface 202 of the solid-state lasing medium 100, passes through the length of the same, travels along beam path 200, reflects off of the intra cavity redirecting optic 203, travels along beam path 206, passes through the Q-switching elements 207, travels along beam path 208, and partially reflects off of surface 209 of the partially reflective optic in an adjustable mount 104. This permits laser emission for a brief interval to form a laser pulse, which is then propagated along the axis denoted by beam 116.

When a pulse of laser radiation is generated by laser oscillator 107 of FIG. 5 and propagated along the axis denoted by beam 116, part of the optical radiation generated may be sampled to facilitate monitoring and control of the present or future laser pulses. The pulse sampling components, operation, and interaction, including elements 165, 118, 119, 130, 128, 129, 131, 132, and 115, remain the same as described in conjunction with FIG. 4 and are not once again described in detail.

After the laser oscillator 107 of FIG. 5 emits a beam 116 of laser radiation, the portion of the beam 116 that is not redirected by partial beam splitter 117 is directed along the axis indicated by beam 120 to the target 127. This direction may be through various means, including direction through one or more optical elements 216, which typically focus beam 120 into a smaller size 217 for entry into a flexible, hollow wave-guide 220, which is of a given fixed or variable size and is suitable for transmittance of the wavelength(s) generated by laser oscillator 107. Flexible, hollow wave-guide 220 is of a conventional type known in the art consisting of: proximal end 219, body 225, distal end 221, and one or more optional distal optical elements 222. The beam 217 is thus directed along the interior of this flexible, hollow wave-guide 220 by both reflecting off of the interior surface of the body 225 as shown by reflected beams 219 and through one or more optional distal optical elements 222, until it exits the flexible, hollow wave-guide 220 as beam 223. This beam 223 may be focused to a small spot, spread out to a large spot, or distributed into an array of spots through the use of one or more optional distal optical elements 222. Beam 223 is directed to the target 127 by repositioning or bending the distal end 221 of the flexible, hollow wave-guide 220 until beam 223 strikes the target 127 at site 224.

Note that the distal end 221 of the flexible, hollow wave-guide 220 may either be in contact with target 127 (not illustrated) or at some distance away from target 127. If the distal end 221 of the flexible, hollow wave-guide 220 is in direct contact with target 127, the optical beam 223 exiting the distal end 221 of the flexible, hollow wave-guide 220 may be either directly transmitted to the target 127 if one or more optional distal optical elements 222 are present at the distal end 221 of the flexible, hollow wave-guide 220 or transmitted through a gaseous medium if none of the optional distal optical elements 222 are present at the distal end 221 of the flexible, hollow wave-guide 220. However, if the distal end 221 of the flexible, hollow wave-guide 220 is not in direct contact with target 127, the optical beam 223 exiting the distal end 221 of the flexible, hollow wave-guide 220 may be transmitted to the target 127 through a gaseous, fluid, and/or solid medium, one or more of which may be preferred to achieve the desired effects on target 127.

Moreover, the effects of the laser beam 223 on the target 127 may be monitored and the various parameters of the beam 223 may be controlled to produce the desired results at the target site 224 using a feedback mechanism. In the embodiment illustrated in FIG. 5, the effects on the target 127 may be monitored by target site 224 feedback through the flexible, hollow wave-guide 220, in a manner similar to that described in combination with FIG. 4 (not illustrated). An aiming beam may also be provided if desired with the embodiment shown in FIG. 5, in a manner similar to that described in connection with FIG. 1, and is not once again described in detail.

It will also be appreciated that additional variations of generating pulse groupings are contemplated by the present invention. FIGS. 6A–6E contain a set of simplified charts showing the pumping, generation, pulse feedback, energy feedback, and target thermal effects of a laser device operating as a function of time, where two pulses of differing energies and peak powers are generated in each pulse grouping also in accordance with the method of the present invention. As previously described, the waveforms in this simplified chart include the optical pumping pulse waveform 251 of FIG. 6A, the output laser pulse waveform 252 of FIG. 6B, a laser pulse feedback waveform 253 of FIG. 6C that is proportional to the shape and timing of the laser pulse delivered in FIG. 6B, a laser energy feedback waveform 254 of FIG. 6D that is proportional to the energy of the laser pulse delivered in FIG. 6B, and the target thermal waveform 255 of FIG. 6E. One can realize through a comparison of the diagrams that the features and operation described in conjunction with FIGS. 3A–3E are very similar to the features and operation of FIGS. 6A–6E, and thus only the differences in the features between FIGS. 3A–3E and FIGS. 6A–6E are subsequently described in detail.

As illustrated in FIG. 6A with regard to the optical pumping pulse waveform 251, the shape, timing, and amplitude of the rising and falling edges 260 of the second optical pump pulse 259, along with the duration of second optical pump pulse 259 itself are nearly identical to those shown for both the rising and falling edges 256 of the first optical pump pulse 257 and the duration of first optical pump pulse 257 itself. This method of generating pulse groupings can be advantageous when it is less complex to generate multiple optical pump pulses that are of nearly the same shape and duration than it is to individually control the shape and timing of each optical pump pulse. This method can also be valuable to produce different, desirable target effects versus having laser pulses of the same shape and duration.

The effect of having nearly identical pump pulses in FIG. 6A is that the resulting laser pulses 274 and 276 in the pulse grouping have different energies, peak powers, pulse widths, and pulse shapes. This is due to the fact that the solid-state lasing medium 100, within the laser oscillator 107, contains one or more lasing ions doped in various concentrations within a host material that have in combination the characteristics of relatively long emission and energy storage lifetimes, which can store optical energy in the interval between optical pumping pulses 258 as previously described. Therefore, the threshold optical pump energy is lower for the second laser pulse 276 than for the first laser pulse 274 and as a result, leads to the differences in output beam characteristics. The second laser pulse 276 in the pulse grouping, in this embodiment, has a wider pulse width, higher total pulse energy, broader pulse shape, and lower peak power than the corresponding first laser pulse 274 in the pulse grouping.

These differences in characteristics between the first and second laser pulses 274 and 276 in the pulse grouping of FIG. 6B also translate to corresponding differences in FIGS. 6C, 6D, and 6E. As depicted in FIG. 6C, the second detected pulse 282 in the laser pulse feedback waveform 253 has the same changes to its waveform as are present in the second laser pulse 276; namely, a wider pulse width, higher total pulse energy, broader pulse shape, and lower peak power. The higher total energy in the detected second pulse 282 translates into a higher total energy detected in the second detected pulse 291 of FIG. 6D. This increase in total pulse energy for the second pulse thus produces a much larger thermal change in the target 127 for the second pulse of the pulse grouping, as illustrated in FIG. 6E by the larger change in temperature 303 and higher peak temperature value 304 than observed in the comparable target thermal waveform segments of FIG. 3E. This much larger thermal change is also seen in FIG. 6E as a difference in temperature changes between temperature rise 300 of the first pulse and temperature rise 303 of the second pulse of the pulse grouping. In this instance, not only does the temperature rise 300 of the first pulse assist in allowing the second pulse to provide an enhanced thermal target effect, but the increase in energy of the second pulse of the pulse grouping can also enhance the target effects achieved by the second pulse in the pulse grouping.

The CPU 115 control of the second grouping of optical pumping pulses, denoted by pump waveform segments 265 through 270 of FIG. 6A, allows the generation of the second grouping of output laser pulses, denoted by pulse waveform segments 271 and 277 through 279 of FIG. 6B. The features and details of operation of the second grouping of laser pulses are similar to the features and details of operation of the first grouping of laser pulses and thus they are not described again in detail. This includes pulse waveform segments 271 and 277 through 279 of the second grouping of output laser pulses in FIG. 6B, pulse feedback waveform segments 272 and 283 through 285 of the second grouping of detected laser pulses in FIG. 6C, energy feedback waveform segments 273 and 293 through 299 of the second grouping of detected laser pulses in FIG. 6D, and target thermal waveform segments 306 through 312 of the second grouping of laser pulses in FIG. 6E. These features are again denoted for clarification that the pulse groupings of laser pulses may be employed in a repetitive manner, although it will be recognized that the present invention may also be employed with a single grouping of laser pulses.

The principles of the method of the present invention can also be applied to the generation and delivery of pulse groupings with more than two pulses per grouping. FIGS. 7A–7E contain simplified charts showing the pumping, generation, pulse feedback, energy feedback, and target thermal effects of a laser device operating as a function of time, where three pulses of approximately equivalent energy and peak power are generated in each pulse grouping in accordance with the method of the present invention. Again, as previously described, the waveforms in this simplified chart include the optical pumping pulse waveform 251 of FIG. 7A, the output laser pulse waveform 252 of FIG. 7B, a laser pulse feedback waveform 253 of FIG. 7C that is proportional to the shape and timing of the laser pulse delivered in FIG. 7B, a laser energy feedback waveform 254 of FIG. 7D that is proportional to the energy of the laser pulse delivered in FIG. 7B, and the target thermal waveform 255 of FIG. 7E. One can realize through a comparison of the charts that the features and operation described in conjunction with FIGS. 3A–3E are very similar to the features and operation of FIGS. 7A–7E, and thus only the differences in the features between FIGS. 3A–3E and FIGS. 7A–7E are subsequently described in detail.

Figures 7A, 7B, 7C, 7D, 7E:
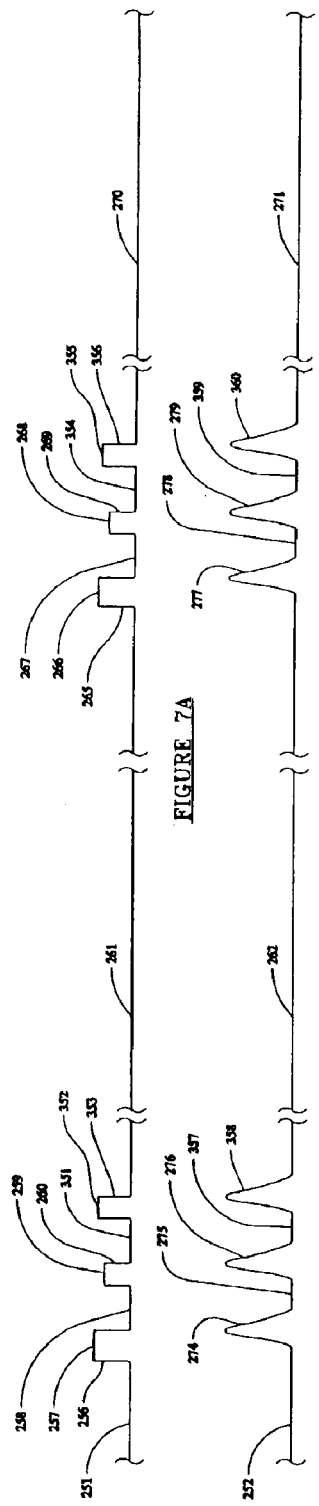
FIGS. 7A–7E are yet another additional set of simplified charts showing the pumping, generation, pulse feedback, energy feedback, and target thermal effects of a laser device operating as a function of time and in accordance with the present invention, where three pulses of approximately equivalent energy and peak power are generated in each pulse grouping.

As depicted in FIG. 7A with regard to the optical pumping pulse waveform 251, several additional features have been included, consisting of an extra interval between pulses 351, further rising and falling edges 353, and an extra amplitude 352 to allow for the delivery of a third optical pumping pulse in the pulse grouping. The values of the shape and timing of this third optical pumping pulse are controlled by CPU 115, in addition to the other parameters of FIG. 7A. These values are controlled, in this depiction of the operation of an embodiment of the present invention, such that the laser pulses 274, 276, and 358 shown in the output laser pulse waveform 252 are both nearly identical in shape and timing, and have nearly identical intervals 275 and 357 between them.

The effect of having different shapes or amplitudes for the optical pumping pulses 257, 259, and 352 in FIG. 7A is that the resulting laser pulses 274, 276, and 358 in the pulse grouping of FIG. 7B have nearly identical characteristics. The need for having different shapes and timing for optical pumping pulses 257, 259, and 352 in FIG. 7A is again due to the fact that the solid-state lasing medium 100, within the laser oscillator 107, contains one or more lasing ions doped in various concentrations within a host material that have in combination the characteristics of relatively long emission and energy storage lifetimes, which can store optical energy in the interval between optical pumping pulses 258 and 352 as previously described. Therefore, the threshold optical pump energy is higher for the first laser pulse 274 than for the second laser pulse 276, and is similar for both the second laser pulse 276 and the third laser pulse 358, that thus lead to the differences in pumping pulse characteristics. Each of the three laser pulses 274, 276, and 358 in FIG. 7B have nearly identical pulse widths, total pulse energies, pulse shapes, and peak powers.

These similarities in characteristics between the first, second, and third laser pulses in the pulse grouping also translate to corresponding similarities in FIGS. 7C, 7D, and 7E. All three detected pulses 280, 282, and 362 in FIG. 7C have nearly identical characteristics, including the intervals 281 and 361 between the detected laser pulses 280, 282, and 362 and energy levels. Because of their nearly identical characteristics, the detected energy levels shown in energy feedback waveform segments 287, 291, and 367 of FIG. 7D are also nearly identical, as well as the interval between laser pulses 289 and 365, rising edges 286, 290, and 366, and falling edges 288, 292, and 368. The nearly identical total pulse energies from all three laser pulses in the pulse grouping allow similar target temperature rises 300, 303, and 374 in FIG. 7E for each of the laser pulses delivered to the target 127. This also includes similar peaks 301, 304, and 375 for the three laser pulses on the target 127 at progressively higher temperatures, as well as similar temperature decay times for the three laser pulses as denoted by target thermal waveform segments 302, 373, and 305. In this instance, the temperature rise 300 of the first pulse and temperature rise 303 of the second pulse assist in allowing the second and third pulses, respectively, to provide an enhanced thermal effect to the target 127.

The CPU 115 control of the second grouping of optical pumping pulses, denoted by pump waveform segments 265 through 270 and 354 through 356 of FIG. 7A, again allows the generation of the second grouping of output laser pulses, denoted by pulse waveform segments 271, 277 through 279, and 359 through 360 of FIG. 7B. The features and details of operation of the second grouping of laser pulses are similar to the features and details of operation of the first grouping of laser pulses and thus they are not described again in detail. This includes pulse waveform segments 271, 277 through 279, and 359 through 360 of the second grouping of output laser pulses in FIG. 7B, pulse feedback waveform segments 272, 283 through 285, and 363 through 364 of the second grouping of detected laser pulses in FIG. 7C, energy feedback waveform segments 273, 293 through 299, and 369 through 372 of the second grouping of detected laser pulses in FIG. 7D, and target thermal waveform segments 306 through 312 and 376 through 378 of the second grouping of laser pulses in FIG. 7E.

Of course, more than three laser pulses may be employed in each grouping of laser pulses in a pulse train by modifying the various components and control system as necessary.

Other modifications of the illustrated embodiments and method of the present invention may be made. It will be appreciated, however, that the present invention provides a novel means for the generation and application of laser pulse trains, constituted by one or more pulse groupings, using selected solid-state lasing media in one or more laser oscillators or resonators. The systems that embody this invention permit a number of pulses of laser energy to be directed to a target in a relatively short time period so as to provide various beneficial target effects, for example, efficiently cutting or ablating tissues of different hardnesses.

It will be readily apparent from the foregoing detailed description of the invention and from the illustrations thereof that numerous variations and modifications may be effected without departing from the true spirit and scope of the novel concepts or principles of this invention.

I claim:

1. A device for generating laser pulse trains for delivery to a target comprising;

a single laser generator for generating and delivering a plurality of laser pulse groupings as a laser pulse train to a target at selected time intervals wherein each of the laser pulse groupings comprises two or more individual successive pulses generated at selected time intervals; and a controller operably associated with the generator for selecting and controlling the time intervals between each of the pulse groupings and each of the individual pulses;

wherein the laser generator has a lasing medium selected from the group consisting of Er:YAG, Tm:YAG, Ho:YAG, Er:YLF, Tm:YLF, Ho:YLF, Er;YSGG, Tm:YSGG, TmHo:YAG, CrTmHo:YAG and ruby, and wherein the laser pulse train has a pulse width of 100 to 800 microseconds and a pulse repetition rate of 1 to 100 Hertz.

2. The device of claim 1 wherein the controller additionally selects and controls the amplitude, duration and shape of each of the individual pulses in each of the laser pulse trains.

3. The device of claim 2 wherein the controller is a central processing unit.

4. The device of claim 1 further comprising a sampling monitor operably associated with the controller for sampling and monitoring the characteristics of the individual pulses generated by the generator.

5. The device of claim 1 wherein the generator is a resonator.

6. The device of claim 1 wherein the generator is an oscillator consisting of a pump chamber housing a solid-state lasing medium having relatively long emission and energy storage lifetime and a flash lamp.

7. The device of claim 1 further comprising a feedback monitor operably associated with the controller for monitoring and controlling the characteristics of the pulses delivered to the target.

8. The device of claim 1 wherein the generator is a continuous-wave pump for pumping a solid-state medium by a semiconductor laser diode source and a Q-switch.

9. The device of claim 1 further including an aiming beam generator.

10. The device of claim 1 wherein the pulse width is 300 microseconds, the pulse repetition rate is 15 Hertz, and pulse spacing within a laser pulse grouping is 0.1 to 10 milliseconds.

11. The device of claim 1 wherein the lasing medium has a host crystal selected from the group consisting of $Y_3Al_5O_{12}$ (YAG), $Y_3Sc_2Ga_3O_{12}$ (YSGG), $LiYF_4$ (YLF), $Gd_3Sc_2Ga_3O_{12}$ (GSGG), $Y_3Ga_5O_{12}$ (YGG), $Y_3AlO_3$ (YAP), $LaF_3$, $BaY_2F_8$, and $KCaF_3$.

* * * * *